(12) United States Patent
Banerjee et al.

(10) Patent No.: US 7,892,854 B2
(45) Date of Patent: Feb. 22, 2011

(54) MULTIANALYTE MOLECULAR ANALYSIS USING APPLICATION-SPECIFIC RANDOM PARTICLE ARRAYS

(75) Inventors: Sukanta Banerjee, North Brunswick, NJ (US); Michael Seul, Fanwood, NJ (US); Alice X. Li, Ithaca, NY (US); Kairali Podual, North Brunswick, NJ (US); Chiu W. Chau, Edison, NJ (US)

(73) Assignee: BioArray Solutions, Ltd., Warren, NJ (US)

( * ) Notice: Subject to any disclaimer, the term of this patent is extended or adjusted under 35 U.S.C. 154(b) by 2496 days.

(21) Appl. No.: 10/204,799

(22) PCT Filed: Jun. 21, 2001

(86) PCT No.: PCT/US01/20179

§ 371 (c)(1),
(2), (4) Date: Feb. 19, 2003

(87) PCT Pub. No.: WO01/98765

PCT Pub. Date: Dec. 27, 2001

(65) Prior Publication Data

US 2004/0132122 A1     Jul. 8, 2004

(51) Int. Cl.
G01N 33/553    (2006.01)
C12Q 1/68      (2006.01)

(52) U.S. Cl. .................. 436/525; 436/518; 536/22.1; 435/6; 435/7.1; 435/283.1; 435/287.2; 435/22.1

(58) Field of Classification Search ............... 436/525, 436/518; 435/6, 7.1, 174, 5, 283.1, 287.2; 536/22.1
See application file for complete search history.

(56) References Cited

U.S. PATENT DOCUMENTS

| 4,873,102 A | 10/1989 | Chang et al. |
| 5,221,417 A | 6/1993 | Basavanhally ............... 156/629 |
| 5,395,688 A | 3/1995 | Wang et al. ................. 428/327 |

(Continued)

FOREIGN PATENT DOCUMENTS

DE         199 40 810 A    5/2000

(Continued)

OTHER PUBLICATIONS

Loomans et al. Journal of Immunological Methods, vol. 184, No. 2, Aug. 18, 1995, pp. 207-217 (11).*

(Continued)

*Primary Examiner*—Jacob Cheu
*Assistant Examiner*—Pensee T. Do
(74) *Attorney, Agent, or Firm*—Womble Carlyle Sandridge & Rice PLLC

(57) ABSTRACT

The present invention provides methods and apparatus for the application of a particle array in bioassay format to perform qualitative and/or quantitative molecular interaction analysis between two classes of molecules (an analyte and a binding agent). The methods and apparatus disclosed herein permit the determination of the presence or absence of association, the strength of association, and/or the rate of association and dissociation governing the binding interactions between the binding agents and the analyte molecules. The present invention is especially useful for performing multiplexed (parallel) assays for qualitative and/or quantitative analysis of binding interactions of a number of analyte molecules in a sample.

14 Claims, 22 Drawing Sheets

U.S. PATENT DOCUMENTS

| | | | | |
|---|---|---|---|---|
| 5,639,603 | A | 6/1997 | Dower et al. | 435/6 |
| 5,648,124 | A | 7/1997 | Sutor | 427/475 |
| 5,660,990 | A | 8/1997 | Rao et al. | |
| 5,751,629 | A | 5/1998 | Nova et al. | 365/151 |
| 5,922,617 | A | 7/1999 | Wang et al. | 436/518 |
| 5,981,180 | A | 11/1999 | Chandler et al. | 435/6 |
| 6,180,226 | B1 | 1/2001 | McArdle et al. | 428/332 |
| 6,251,691 | B1 | 6/2001 | Seul | 436/534 |
| 6,268,222 | B1 | 7/2001 | Chandler et al. | 436/523 |
| 6,280,618 | B2 | 8/2001 | Watkins | |
| 6,514,714 | B1 | 2/2003 | Lee et al. | |
| 6,620,584 | B1 * | 9/2003 | Chee et al. | 435/6 |
| 6,942,968 | B1 * | 9/2005 | Dickinson et al. | 435/6 |
| 6,993,156 | B1 * | 1/2006 | Szeliski et al. | 382/103 |
| 2001/0046602 | A1 | 11/2001 | Chandler et al. | 428/403 |
| 2002/0022276 | A1 | 2/2002 | Zhou et al. | |
| 2002/0081714 | A1 | 6/2002 | Jain et al. | |
| 2003/0012693 | A1 | 1/2003 | Otillar et al. | |
| 2003/0012699 | A1 | 1/2003 | Moore et al. | |
| 2003/0022370 | A1 | 1/2003 | Casagrande et al. | |
| 2003/0040129 | A1 | 2/2003 | Shah | |
| 2004/0009614 | A1 | 1/2004 | Ahn et al. | |
| 2004/0021073 | A1 | 2/2004 | Barbic et al. | |
| 2004/0106121 | A1 | 6/2004 | Ugolin et al. | |

FOREIGN PATENT DOCUMENTS

| | | |
|---|---|---|
| WO | WO 91/09141 | 6/1991 |
| WO | WO 96/30392 | 10/1996 |
| WO | WO 97/40385 | 10/1997 |
| WO | WO 98/53093 | 11/1998 |
| WO | WO 00/31356 | 6/2000 |
| WO | WO 01/20593 | 3/2001 |
| WO | WO 03/058196 | 7/2003 |
| WO | WO 03/058196 A2 | 7/2003 |

OTHER PUBLICATIONS

European Search Report, Feb. 3, 2004.

Liakopoulos et al., A Bio-Magnetic Bead Separator On Glass Chips Using Semi-encapsulated Spiral Electromagnets.

Yellen et al., Statistical Analysis of Weakest Link in Chains of Magnetic Particle Carriers for Applications in Printing Biochemical Arrays, European Cells and Materials vol. 3: 88-91 (2002).

McCloskey et al., Magnetophoretic Mobilities Correlate to Antibody Binding Capacities, Cytometry vol. 40: 307-315 (2000).

Fuh et al., A Method for Determination of Particle Magnetic Susceptibility with Analytical Magnetapheresis, Anal. Chem. vol. 72: 3590-3595 (2000).

McCloskey et al., Magnetic Cell Separation: Characterization of Magnetophoretic Mobility, Anal. Chem. vol. 75: 6868-6874 (2003).

Richardson et al., A novel measuring system for the determination of paramagnetic particle labels for use in magneto-immunoassays, Biosensors & Bioelectronics vol. 16: 1127-1132 (2001).

Richardson et al., The use of coated paramagnetic particles as a physical label in a magneto-immunoassay, Biosensors & Bioelectronics vol. 16: 989-993 (2001).

Zborowski et al., Continuous cell separation using novel magnetic quadrupole flow sorter, Journal of Magnetism and Magnetic Materials vol. 194: 224-230 (1999).

Moore et al., The use of magnetite-doped polymeric microspheres in calibrating cell tracking velocimetry J. Biochem. Biophys. Methods vol. 44: 115-130 (2000).

Chalmers et al., An instrument to determine the magnetophoretic mobility of labeled, biological cells and paramagnetic particles, Journal of Magnetism and Magnetic Materials vol. 194: 231-241 (1999).

Sun et al., Continuous, Flow-Through Immunomagnetic Cell Sorting in a Quadrupole Field, Cytometry vol. 33: 469-475 (1998).

Gates et al., Photonic Crystals That Can Be Addressed with an External Magnetic Field, Adv. Mater. vol. 13 No. 21: 1605-1608 (2001).

Reddy et al., Determination of the Magnetic Susceptibility of Labeled Particles by Video Imaging, Chemical Engineering Science, vol. 51, No. 6: 947-956 (1996).

Choi et al., An on-chip magnetic separator using spiral electromagnets with semi-encapsulated permalloy, Biosensors & Bioelectronics vol. 16: 409-416 (2001).

Wilson et al. "A new microsphere-based immunoflourescence assay for antibodies to membrane-associated antigens". *Journal of Immunological Methods*. vol. 107: 231-237 (1988).

* cited by examiner

Bead 1             Bead 2

Ligand 1

Ligand 2

MULTIANALYTE MOLECULAR ANALYSIS USING APPLICATION-SPECIFIC RANDOM PARTICLE ARRAYS

FIELD OF THE INVENTION

The present invention relates to multiplexed bioassays for analyzing binding interactions between analytes and binding agents, including methods for determining the affinity constants and kinetic properties associated with analyte-binding agent interactions.

BACKGROUND OF THE INVENTION

The imprinting of multiple binding agents such as antibodies and oligonucleotides on planar substrates in the form of spots or stripes facilitates the simultaneous monitoring of multiple analytes such as antigens and DNA in parallel ("multiplexed") binding assays. The miniaturization of this array format for increasing assay throughput and studying binding kinetics are described, for example, in R. Ekins, F. W. Chu, Clin. Chem. 37, 955-967 (1991); E. M. Southern, U. Maskos, J. K. Elder, Genomics 13, 1008-1017 (1992). In recent years, this approach has attracted substantial interest particularly in connection with performing extensive genetic analysis, as illustrated in G. Ramsay, Nat. Biotechnol. 16, 40-44 (1998); P. Brown, D. Botstein, Nat. Genet. 21, 33-37 (1999); D. Duggan, M. Bittner, Y. Chen, P. Meltzer, J. M. Trent, Nat. Genet. 21, 10-14 (1999); R. Lipshutz, S. P. A. Fodor, T. R. Gingeras, D. J. Lockhart, Nat. Genet. 21, 20-24 (1999).

The principal techniques of array fabrication reported to date include: refinements of the original "spotting" in the form of pin transfer or ink jet printing of small aliquots of probe solution onto various substrates, as illustrated in V. G. Cheung, et al., Nat. Genet. 21, 15-19 (1999); sequential electrophoretic deposition of binding agents in individually electrically addressable substrate regions, as illustrated in J. Cheng, et al., Nat. Biotechnol., 541-546 (1998); and methods facilitating spatially resolved in-situ synthesis of oligonucleotides, as illustrated in U. Maskos, E. M. Southern, Nucleic Acids Res. 20, 1679-1684 (1992); S. P. A. Fodor, et al., Science 251, 767-773 (1991) or copolymerization of oligonucleotides, as illustrated in A. V. Vasiliskov, et al., BioTechniques 27, 592-606 (1999). These techniques produce spatially encoded arrays in which the position within the array indicates the chemical identity of any constituent probe.

The reproducible fabrication of customized arrays by these techniques requires the control of microfluidics and/or photochemical manipulations of considerable complexity to ensure consistent performance in quantitative assays. Microfluidic spotting to produce, in quantitatively reproducible fashion, deposited features of 100 µm diameter involves dispensing of nanoliter aliquots with tight volume control, a task that exceeds the capabilities of currently available fluid handling methodologies. In addition, exposure of binding agents to air during the deposition process, typically several hours' in duration, has uncontrollable impact on the molecular configuration and the accessibility of the binding agents in subsequent binding assays. In-situ array synthesis relies on a sequence of multiple masking and photochemical reaction steps which must be redesigned to accommodate any changes in array composition. Finally, assay performance must be assessed "in-situ" for each array subsequent to immobilization of binding agents, an aspect of array manufacturing which raises difficult quality control and implementation issues.

SUMMARY OF THE INVENTION

The present invention provides methods and apparatus for the application of a particle array in bioassay format to perform qualitative and/or quantitative molecular interaction analysis between two classes of molecules (an analyte and a binding agent). The methods and apparatus disclosed herein permit the determination of the presence or absence of association, the strength of association, and/or the rate of association and dissociation governing the binding interactions between the binding agents and the analyte molecules. The present invention is especially useful for performing multiplexed (parallel) assays for qualitative and/or quantitative analysis of binding interactions.

The terms "analyte" and "binding agent" refer to molecules involved in binding interactions. In one example, analyte and binding agent include DNA or RNA fragments (e.g., oligonucleotide), and binding of those fragments to their complementary sequences (hybridization) is analyzed. In another example, binding interactions between ligands and receptors are analyzed. Examples of analytes and binding agents also include aptamers, peptides and proteins (e.g., antibodies), antigens, and small organic molecules.

The term "particles" refer to colloidal particles, including beaded polymer resins ("beads").

The present invention also provides automated, on-demand fabrication of planar arrays composed of a selected mixture of chemically distinct beads (e.g., encoded beads) which are disposed on a substrate surface in accordance with a selected spatial configuration, as described above. In this approach, the beads are functionized to display binding agents. For example, the binding agents may be attached to the beads, preferably by covalent bond. The subsequent quality control and performance evaluation are conducted off-line and are independent from the process of array assembly. The separation of steps such as bead encoding, functionalization and testing; substrate design, processing and evaluation; custom assembly of application-specific arrays; and on-line decoding of arrays enable an otherwise elusive combination of flexibility, reliability and low cost by permitting systematic process control.

The methods disclosed herein permit rapid customization of DNA or protein arrays without the need for process redesign and avoid problems contributing to spot-to-spot as well as chip-to-chip variability. Furthermore, the bead array format permits chip-independent characterization of beads as well as optimization of assay conditions. In addition, multiple bead arrays can be formed simultaneously in discrete fluid compartments maintained on the same chip, permitting the concurrent processing of multiple samples.

BRIEF DESCRIPTION OF DRAWINGS

Other objects, features and advantages of the invention discussed in the above brief explanation will be more clearly understood when taken together with the following detailed description of an embodiment which will be understood as being illustrative only, and the accompanying drawings reflecting aspects of that embodiment, in which.

DETAILED DESCRIPTION OF THE PREFERRED EMBODIMENTS

The fabrication of application-specific bead arrays may involve multiple processes in a multi-step sequence which may be automated using existing liquid handling technology and laboratory automation. The process of Random Encoded Array Detection (READ) includes the fabrication of custom bead arrays as well as the use of such arrays in bioassays, including assays involving multiplexed molecular interaction analysis of analyte and binding agent molecules, including DNA and protein analysis.

Figure 1:
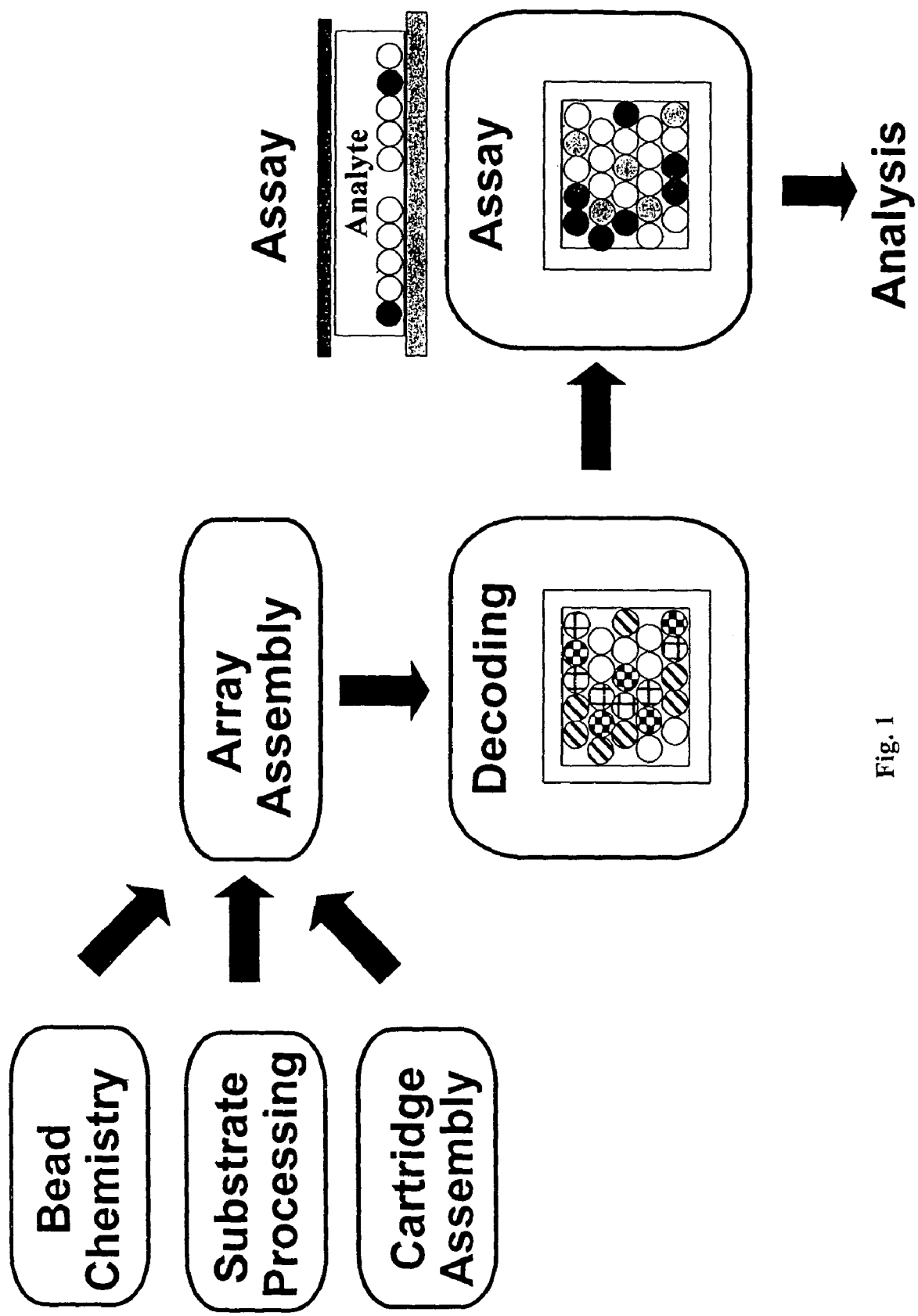
FIG. 1 is an illustration of process flow including the production of random encoded bead arrays and their use in multiplexed assays

FIG. 1 provides a schematic overview of the functional components and process flow by which custom bead arrays may be prepared and used in performing multiplexed biomolecular analysis according to the present invention. The array is prepared by employing separate batch processes to produce application-specific substrates (e.g., chip at the wafer scale) and to produce beads that are chemically encoded and biologically functionalized (e.g., at the scale of ~10^8 beads/100 µl of suspension). The beads subjected to respective quality control (QC) steps prior to array assembly, such as the determination of morphological and electrical characteristics. In addition, actual assays are performed on beads in suspension, before they are introduced to the substrate, to optimize assay conditions, generally with the objective to maximize assay sensitivity and specificity and to minimize bead-to-bead variations. For substrates, QC steps may include optical inspection, ellipsometry and electrical transport measurements.

Once the chemically encoded and biologically functionalized beads are combined with the substrate (e.g., chip), the Light-controlled Electrokinetic Assembly of Particles near Surfaces (LEAPS) may be used for rapid assembly of dense arrays on a designated area on the substrate within the same fluidic phase, avoiding problems contributing to spot-to-spot as well as chip-to-chip variability without the need for retooling or process redesign. Furthermore, the bead array format permits chip-independent characterization of beads as well as optimization of assay conditions. In addition, multiple bead arrays can be formed simultaneously in discrete fluid compartments maintained on the same chip. Once formed, these multiple bead arrays may be used for concurrent processing of multiple samples. The integration of LEAPS with microfluidics produces a self-contained, miniaturized, optically programmable platform for parallel protein and DNA analysis. LEAPS refers to methods of moving particles suspended in the interface between an electrolyte solution and an electrode and is described in U.S. patent application Ser. No. 09/171,550 (also PCT International Application No. PCT/US97/08159) entitled Light-controlled Electrokinetic Assembly of Particles near Surfaces, which is incorporated herein by reference in its entirety. Also incorporated herein by reference in its entirety is U.S. patent application Ser. No. 09/397,793 (also PCT International Application PCT/US00/25466), entitled "System and Method for Programmable Pattern Generation.

In certain embodiments of the present invention, chemical encoding may be accomplished by staining beads with sets of optically distinguishable tags, such as those containing one or more fluorophore dyes spectrally distinguishable by excitation wavelength, emission wavelength, excited-state lifetime or emission intensity. The optically distinguishable tags made be used to stain beads in specified ratios, as disclosed, for example, in Fulwyler, U.S. Pat. No. 4,717,655 (Jan. 5, 1988). Staining may also be accomplished by swelling of particles in accordance with methods known to those skilled in the art, [Molday, Dreyer, Rembaum & Yen, J. Mol Biol 64, 75-88 (1975); L. Bangs, "Uniform latex Particles, Seragen Diagnostics, 1984]. For example, up to twelve types of beads were encoded by swelling and bulk staining with two colors, each individually in four intensity levels, and mixed in four nominal molar ratios. Combinatorial color codes for exterior and interior surfaces is disclosed in International Application No. PCT/US 98/10719, which is incorporated herein by reference in its entirety.

Figure 2:
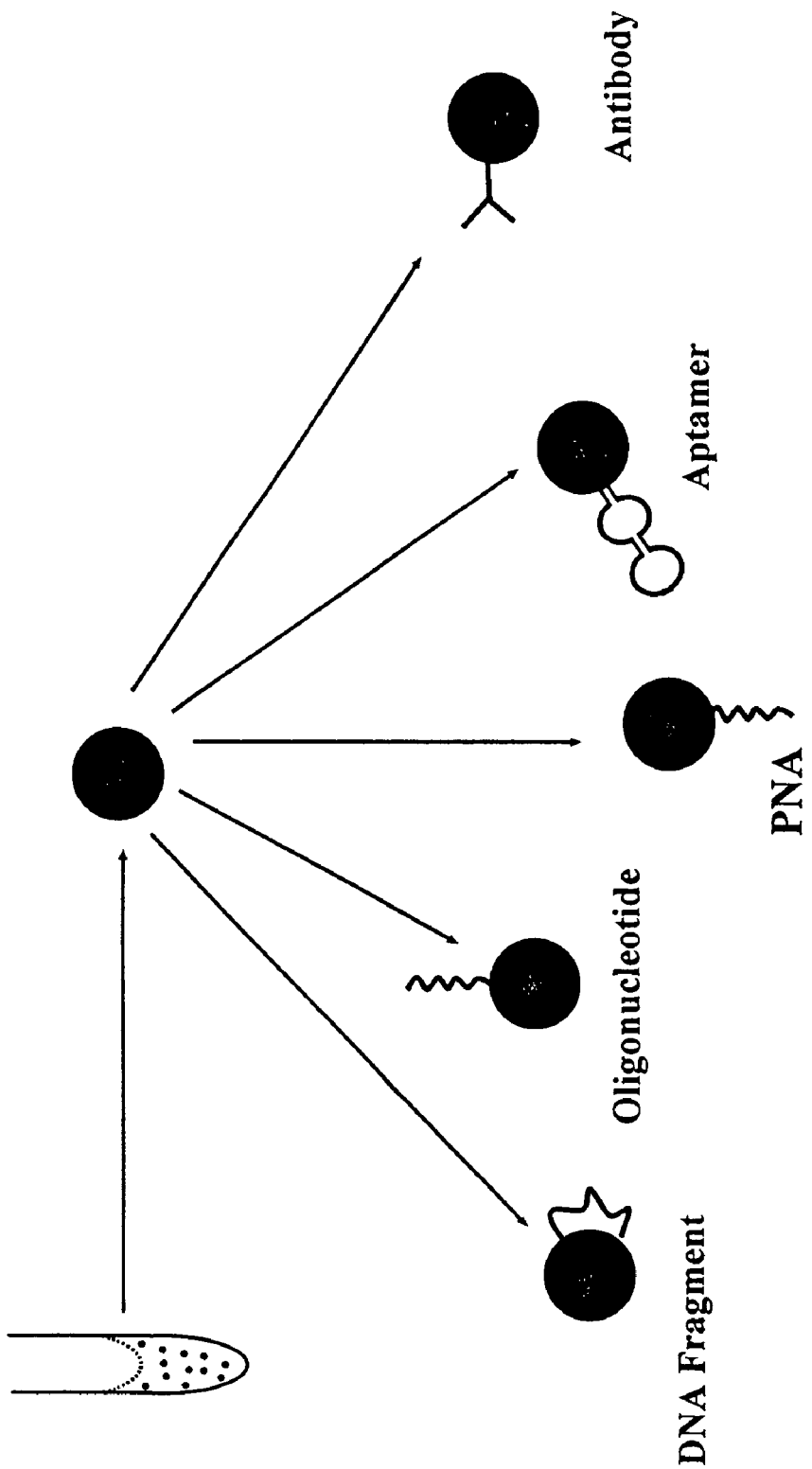
FIG. 2 is an Illustration of the functionalization of beads

Beads are functionalized by binding agent molecules attached thereto, the molecule including DNA (oligonucleotides) or RNA fragments, peptides or proteins, aptamers and small organic molecules in accordance processes known in the art, e.g., with one of several coupling reactions of the known art (G. T. Hermanson, *Bioconjugate Techniques* (Academic Press, 1996); L. Illum, P. D. E. Jones, *Methods in Enzymology* 112, 67-84 (1985). In certain embodiments of the invention, the functionalized beads have binding agent molecules (e.g., DNA, RNA or protein) covalently bonded to the beads. Beads may be stored in a buffered bulk suspension until needed. Functionalization typically requires one-step or two-step reactions which may be performed in parallel using standard liquid handling robotics and a 96-well format to covalently attach any of a number of desirable functionalities to designated beads, as illustrated in FIG. 2. In a preferred embodiment, beads of core-shell architecture will be used, the shell composed in the form of a thin polymeric blocking layer whose preferred composition is selected; and functionalization performed in accordance with the targeted assay application, as known in the art. Samples may be drawn for automated QC measurements. Each batch of beads provides material for hundreds of thousands of chips so that chip-to-chip variations are minimized.

Figure 3:
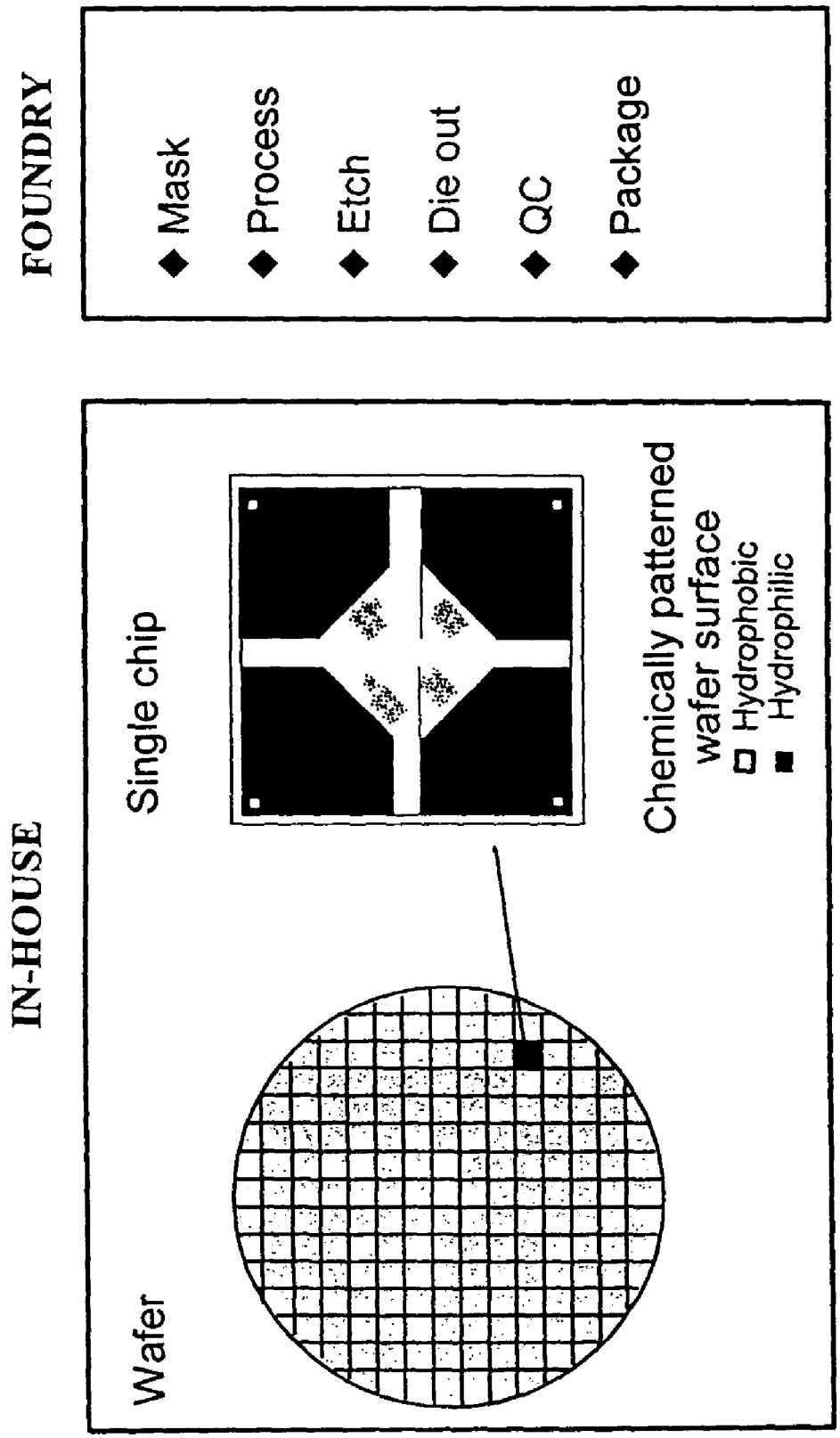
FIG. 3 is an illustration of steps in chip design and wafer-scale production
Figure 4:
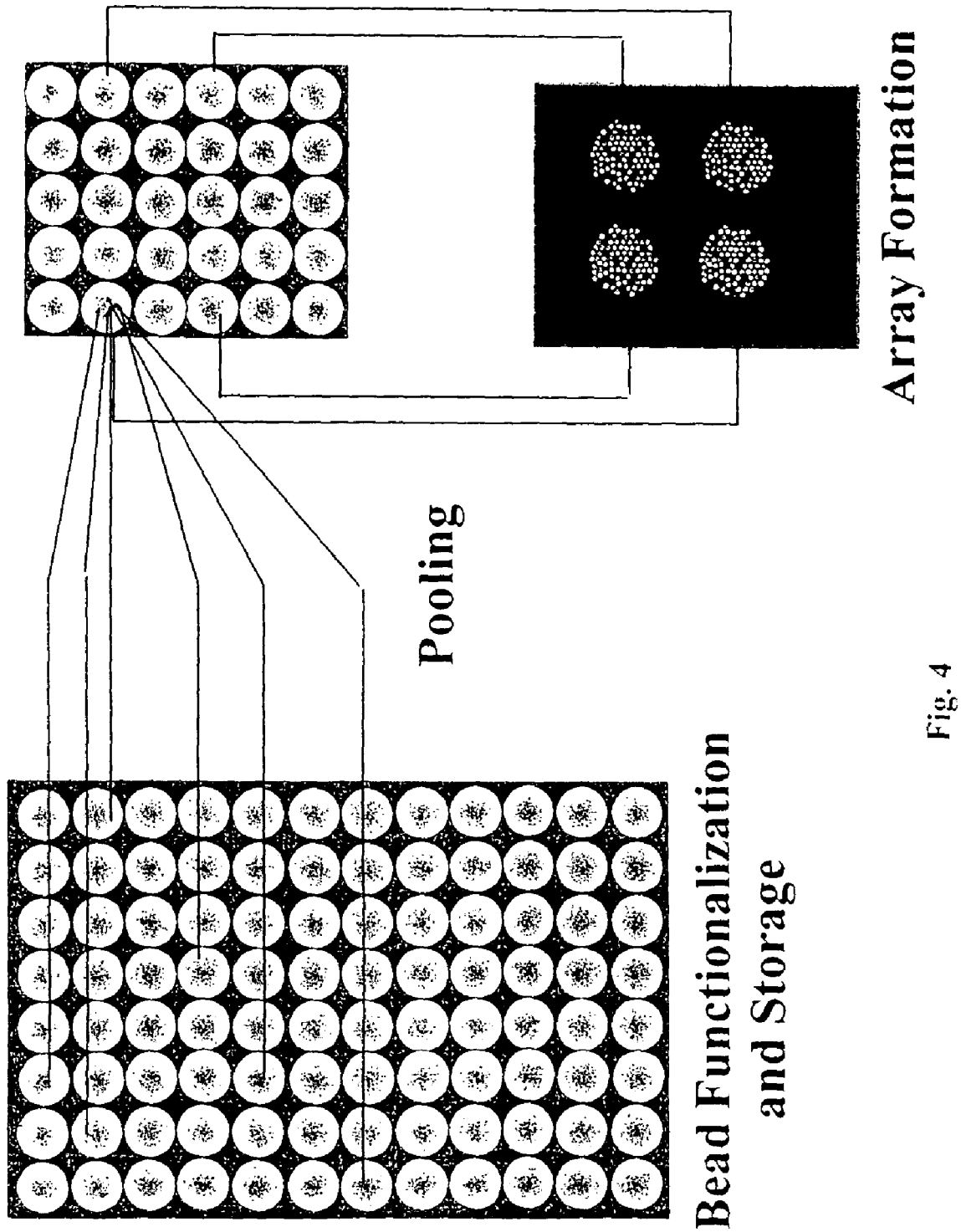
FIG. 4 is an illustration of on-demand assembly of random encoded arrays

Substrates (e.g., chips) used in the present invention may be patterned in accordance with the interfacial patterning methods of LEAPS by, e.g., patterned growth of oxide or other dielectric materials to create a desired configuration of impedance gradients in the presence of an applied AC electric field. Patterns may be designed so as to produce a desired configuration of AC field-induced fluid flow and corresponding particle transport. Substrates may be patterned on a wafer scale by invoking semiconductor processing technology, as illustrated in FIG. 3. In addition, substrates may be compartmentalized by depositing a thin film of a UV-patternable, optically transparent polymer to affix to the substrate a desired layout of fluidic conduits and compartments to confine fluid in one or several discrete compartments, thereby accomodating multiple samples on a given substrate.

In certain embodiments of the invention, the bead array is prepared by providing a first planar electrode that is in substantially parallel to a second planar electrode ("sandwich" configuration) with the two electrodes being separated by a gap and containing an electrolyte solution. The surface or the interior of the second planar electrode is patterned with the interfacial patterning method. Encoded and functionalized beads are introduced into the gap. When an AC voltage is applied to the gap, the beads form a random encoded array on the second electrode (e.g., "chip"). And, also using LEAPS, an array of beads may be formed on a light-sensitive electrode ("chip"). Preferably, the sandwich configuration described above is also used with a planar light sensitive electrode and another planar electrode. Once again, the two electrodes are separated by the a gap and contain an electrolyte solution. The functionalized and encoded beads are introduced into the gap. Upon application of an AC voltage in combination with a light, the beads form an array on the light-sensitive electrode.

In certain embodiments, the application-specific bead arrays useful in the present invention may be produced by picking aliquots of designated encoded beads from individual reservoirs in accordance with the specified array composition and "pooled"; aliquots of pooled suspension are dispensed onto selected substrate (e.g., chips) in a manner preventing the initial fusion of aliquots. Aliquots form a multiplicity of planar random subarrays of encoded beads, each subarray representing beads drawn from a distinct pool and the physical array layout uniquely corresponding to the identity of aliquots drawn from pooled bead populations.

Planar arrays or assemblies of encoded on a substrate which are chemically or physically encoded may be used. To this, spatial encoding may also be added to increase the number of assays that may be conducted. Spatial encoding, for example, can be accomplished within a single fluid phase in the course of array assembly by invoking Light-controlled Electrokinetic Assembly of Particles near Surfaces (LEAPS) to assemble planar bead arrays in any desired configuration in response to alternating electric fields and/or in accordance with patterns of light projected onto the substrate. LEAPS creates lateral gradients in the impedance of the interface between silicon chip and solution to modulate the electrohydrodynamic forces that mediate array assembly. Electrical requirements are modest: low AC voltages of typically less than $10V_{pp}$ are applied across a fluid gap of typically 100 µm between two planar electrodes. This assembly process is rapid and it is optically programmable: arrays containing thousands of beads are formed within seconds under electric field. The formation of multiple subarrays, can also occur in multiple fluid phases maintained on a compartmentalized chip surface.

The multiplexed assays of the present invention may also be performed using beads encoded beads that are assembled, but not in an array, on the substrate surface. For example, by spotting bead suspensions into multiple regions of the substrate and allowing beads to settle under gravity, assemblies of beads can be formed on the substrate. In contrast to the bead arrays formed by LEAPS, these assemblies generally assume low-density, disorder configurations. However, the combination of spatial and color encoding attained by spotting mixtures of chemically encoded beads into a multiplicity of discrete positions on the substrate still provides a degree of multiplexing that is sufficient for certain biological assays.

Binding interaction between the binding agent on those beads and an analyte may be performed either before or after the encoded array is assembled on the substrate. For example, the bead array may be formed after the assay, subsequent to which an assay image and a decoding image may be taken of the array. Alternatively, the beads may be assembled in an array and immobilized by physical or chemical means to produce random encoded arrays, e.g., with the appearance of the array shown in FIG. 10. The arrays may be immobilized, for example, by application of a DC voltage to produce random encoded arrays with the appearance of the array shown in FIG. 10. The DC voltage, set to typically 5-7 V (for beads in the range of 2-6 µm and for a gap size of 100-150 µm) and applied for <30 s in "reverse bias" configuration so that an n-doped silicon substrate would form the anode, causes the array to be compressed to an extent facilitating contact between adjacent beads within the array and simultaneously causes beads to be moved toward the region of high electric field in immediate proximity of the electrode surface. Once in sufficiently close proximity, beads are anchored by van der Waals forces mediating physical adsorption. This adsorption process is facilitated by providing on the bead surface a population of "tethers" extending from the bead surface; polylysine and streptavidin have been used for this purpose.

In certain embodiments, the particle arrays may be immobilized by chemical means, e.g, by forming a composite gel-particle film. In one exemplary method for forming such gel-composite particle films, a suspension of microparticles is provided which also contain all ingredients for subsequent in-situ gel formation, namely monomer, crosslinker and initiator. The particles are assembled into a planar assembly on a substrate by application of LEAPS, e.g., AC voltages of 1-20 $V_{p-p}$ in a frequency range from 100's of hertz to several kilohertz are applied between the electrodes across the fluid gap. Following array assembly, and in the presence of the applied AC voltage, polymerization of the fluid phase is triggered by thermally heating the cell ~40-45° C. using an IR lamp or photometrically using a mercury lamp source, to effectively entrap the particle array within a gel. Gels may be composed of a mixture of acrylamide and bisacrylamide of varying monomer concentrations from 20% to 5% (acrylamide:bisacrylamide=37.5:1, molar ratio), or any other low viscosity water soluble monomer or monomer mixture may be used as well. Chemically immobilized functionalized microparticle arrays prepared by this process may be used for a variety of bioassays, e.g., ligand receptor binding assays.

In one example, thermal hydrogels are formed using azodiisobutyramidine dihydrochloride as a thermal initiator at a low concentration ensuring that the overall ionic strength of the polymerization mixture falls in the range of ~0.1 mM to 1.0 mM. The initiator used for the UV polymerization is Irgacure 2959® (2-Hydroxy-4'-hydroxyethoxy-2-methylpropiophenone, Ciba Geigy, Tarrytown, N.Y.). The initiator is added to the monomer to give a 1.5% by weight solution.

In certain embodiments, the particle arrays may be immobilized by mechanical means. For example, an array of microwells may be produced by standard semiconductor processing methods in the low impedance regions of the silicon substrate. The particle arrays may be formed using such structures by, e.g., utilizing LEAPS mediated hydrodynamic and ponderomotive forces are utilized to transport and accumulate particles on the hole arrays. The A.C. field is then switched off and particles are trapped into microwells and thus mechanically confined. Excess beads are removed leaving behind a geometrically ordered random bead array on the substrate surface.

When the bead array is immobilized before the assay, the array functions as a two-dimensional affinity matrix which displays receptors or binding agents (e.g., oligonucleotides, cDNA, aptamers, antibodies or other proteins) to capture analytes or ligands (DNA, proteins or other small cognate ligands) from a solution that is brought in contact with the array. The bead array platform may be used to perform multiplexed molecular analysis, such as, e.g., genotyping, gene expression profiling, profiling of circulation protein levels and multiplexed kinetic studies.

Figure 5:
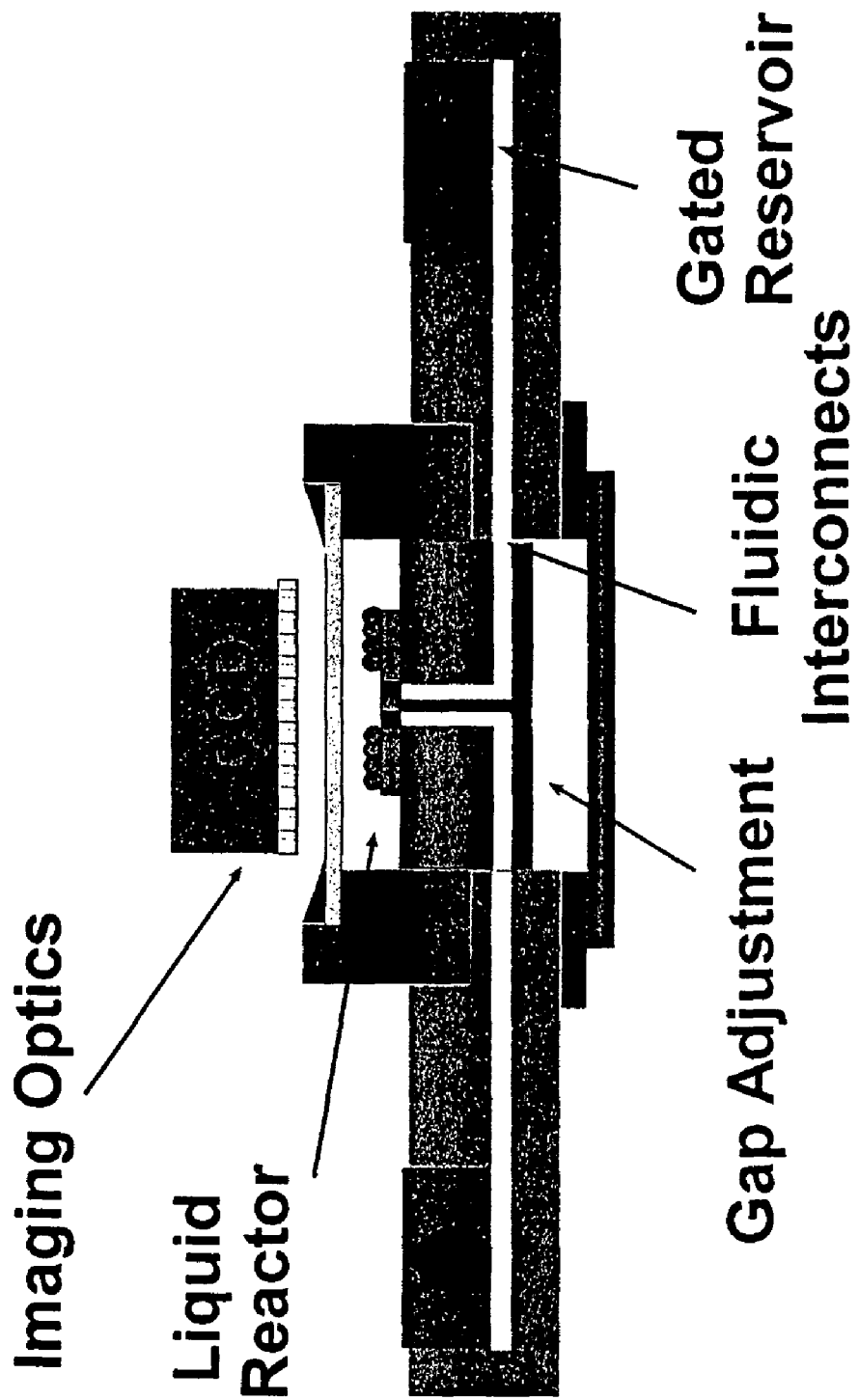
FIG. 5 is an illustration of palmtop microlab
Figure 6:
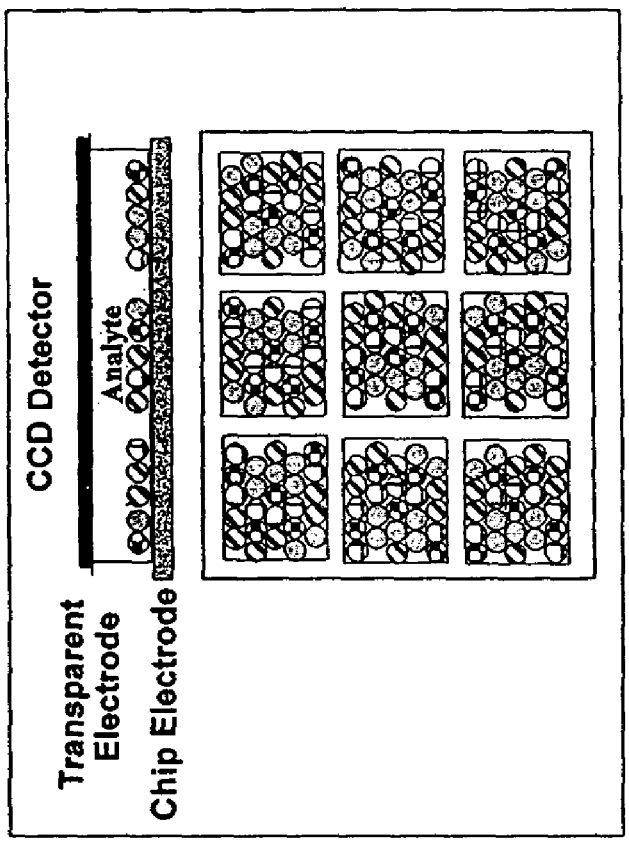
FIG. 6 is a schematic illustration of assay and decoding images used in READ process
Figure 6:
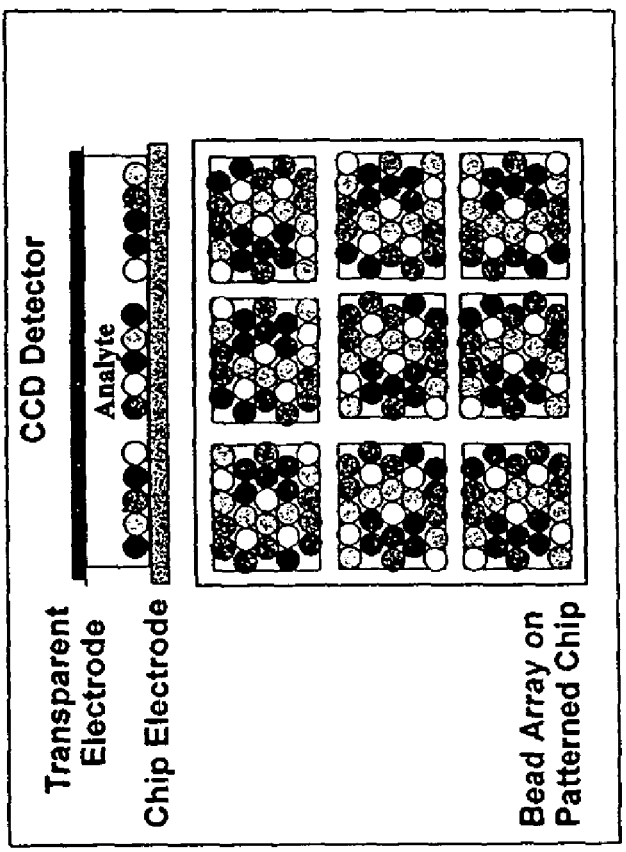

Substrates (e.g., chips) can be placed in one or more enclosed compartment, permitting samples and reagents to be transported in and out of the compartments through fluidic interconnection. On-chip immunoassays for cytokines, e.g., interleukin (IL-6) may be performed in this format. Serum sample and fluorescent labeled secondary antibodies are introduced to the reaction chamber sequentially and allowed to react with beads immobilized on the chip. FIG. 5 illustrates a design of a reaction chamber which may be used in the multiplexed assays according to the present invention. Reactions can also be performed in an open compartment format similar to microtiter plates. Reagents may be pipetted on top of the chip by robotic liquid handling equipment, and multiple samples may be processed simultaneously. Such a format accommodates standard sample processing and liquid handling for existing microtiter plate format and integrates sample processing and array detection.

In certain embodiments, the presence of the analyte-binding agent interactions are associated with changes in the optical signatures of beads involved in the interactions and these optical changes detected and analyzed. The identities of the binding agents involved in the interactions are determined by detecting the chemically or physically distinguishable characteristic associated with those beads. Preferably, chemically distinguishable characteristics include chemical molecules including flurophore dyes, chromophores and other chemical molecules that are used for purposes of detection in binding assays.

The detection of the chemically or physically distinguishable characteristic and the detecting of the optical signature changes associated with the binding interactions may be performed while the particles are assembled in a planar array on a substrate, e.g., by taking an assay and a decoding image of the array and comparing the two, e.g., comparing of the assay and the decoding image comprises use of optical microscopy apparatus including an imaging detector and computerized image capture and analysis apparatus. The decoding image may be taken to determine the chemically and/or physically distinguishable characteristic that uniquely identifies the binding agent displayed on the bead surface, e.g., determining the identity of the binding agents on each particle in the array by the distinguishable characteristic. The assay image of the array is taken to detect the optical signature of the binding agent and the analyte complex. In certain embodiments, fluorescent tags (fluorophore dyes) may be attached to the analytes such that when the analytes are bound to the beads, the flourescent intensities change, thus providing changes in the optical signatures of the beads. In certain embodiments, the decoding image is taken after the beads are assembled in an array and immobilized and before taking the assay image, preferably before contacting the binding agents on the beads with an analyte. In certain other examples, the binding interactions occur while the beads are in solution, and assembled into an array afterwards and the decoding and assay images are obtained. The identity of the binding agent of the binding agent-analyte complex is carried out by comparing the decoding image with the assay image.

Figure 7:
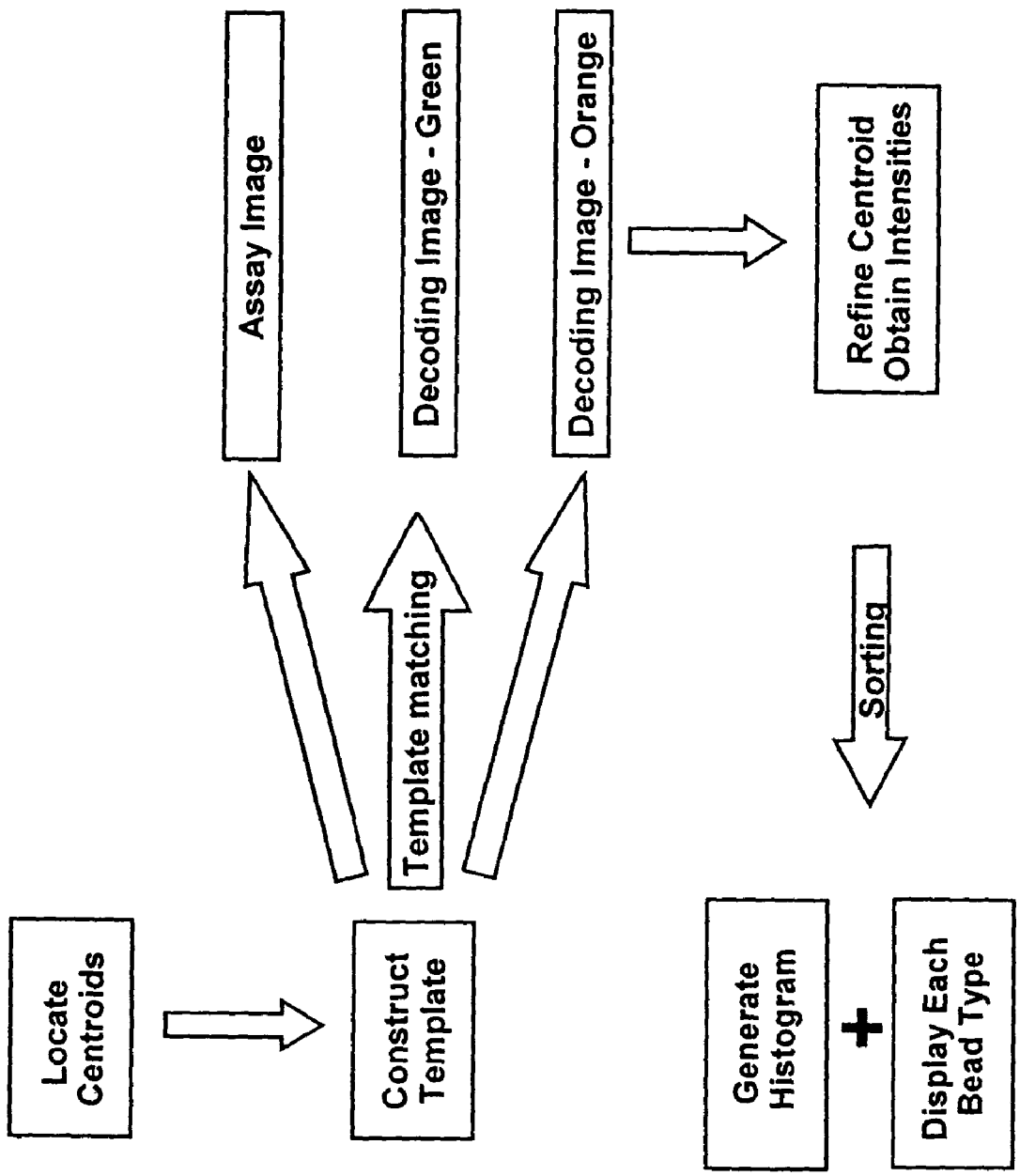
FIG. 7 is a flow chart summarizing algorithms and steps in the analysis of images
Figure 8:
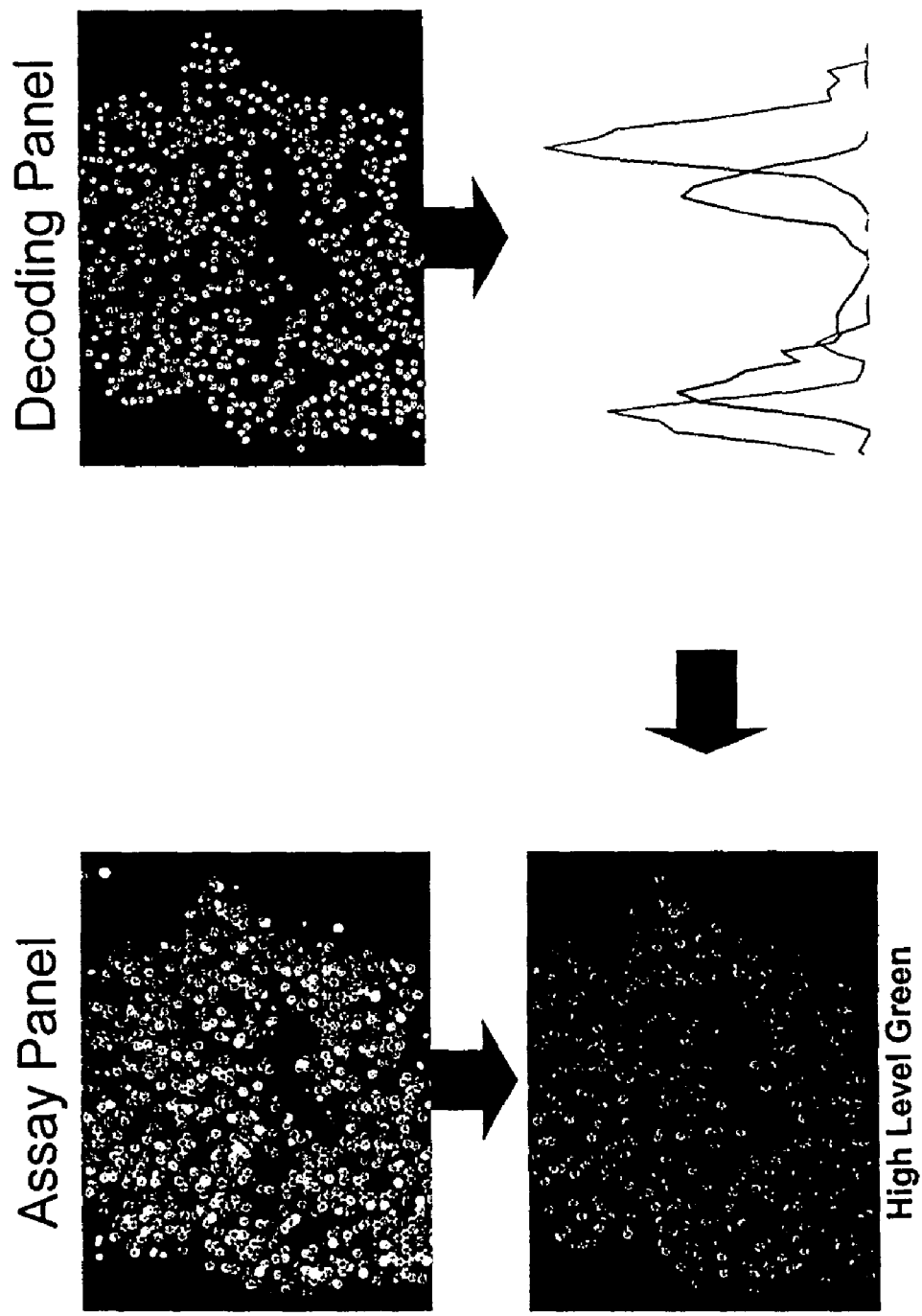
FIG. 8 is an illustration of steps in the decomposition of assay images according to bead type by application of the image analysis algorithm summarized in FIG. 7.

In preferred embodiments, images analysis algorithms that are useful in analyzing the data obtained from the decoding and the assay images. These algorithm may be used to obtain quantitative data for each bead within an array. As summarized in FIG. 7, the analysis software automatically locates bead centers using a bright-field image of the array as a template, groups beads according to type, assigns quantitative intensities to individual beads, rejects "blemishes" such as those produced by "matrix" materials of irregular shape in serum samples, analyzes background intensity statistics and evaluates the background-corrected mean intensities for all bead types along with the corresponding variances.

The methods of the present invention may be used for determining the association and the dissociation constants e.g., by introducing the analyte in a time-dependent manner and analyzing the binding as a function of time, or by washing away the bound analyte in a time-dependent manner and also analyzing the binding as a function of time.

The methods of the present invention may be used for determining the affinity constants of analyte-binding agent interactions, for determining the number of analyte-binding agent complexes formed The present invention also provides methods for determining the concentration of an analyte in a biological sample.

The methods of the present invention may also be used to determining elements of a co-affinity matrix of a given analyte against a panel of binding agents. In one example, the extent of the interaction between the analyte and the binding agents in a panel in competitive, multiconstituent equilibrium reaction may be determined. Determination of co-affinity constants provides useful applications, as described below.

The successful rate of transplantation for several types of organs directly relates to compatibility of Human Leukocyte Antigen (HLA) between donor and recipient. Serological testing of the recipients for the Panel Reactive Antibodies (PRA) is one of the crucial steps to avoid possible rejections. Cross-reaction in PRA testing is a very common phenomenon due to similarity of some HLA antigen structures and the nature of development of these antibodies. In fact, HLA antigens can be organized into groups based on apparent serological cross-reactivity between the groups. These groups are termed Cross-Reactive-Groups (CREGs). In current clinical setting, antibodies from a patient are tested against different antigens in individual reactions. Although a reactive pattern of the antibodies can be generated combining the results from different reactions, the competitive nature of interactions between different antibodies and antigens is not reflected in such a pattern. In other cases, several antigens are mixed together for a binding assay. Lack of identification of each antigen in the system prevents generation of a binding profile.

The result is only the averaged signal from several antigens. In the bead array system, a panel of different antigens is presented to the antibody analytes in a competitive binding environment, and each antigen can be identified through its association with different types of beads. Thus, binding intensity on each antigen in the competitive reactions can be extracted in a single assay. This co-affinity matrix system will provide binding profiles for the CREGs and greatly advance the understanding of the nature of the reaction and improve the accuracy for the related clinical decisions. For example, a N-antibody and M-antigen system provides a matrix of N×M of possible reactions. It is possible to determine K–nm, the affinity constant governing the interaction between the nth antibody against the mth antigen, where m=1, 2, . . . M, and n=1, 2, . . . N. For applications where absolute co-affinity constants are not needed, binding profile will be generated for various antibodies in accordance with the methods of the present invention and results from a patient sample can be matched to these profiles or combination of these profiles.

Co-affinity matrix may also be used to characterize the analyte. For example, combination of the coefficients of the co-affinity matrix and known concentrations of analyte and binding agents participating in the formation of analyte-binding agent complexes serves to define a competitive binding interaction descriptor, e.g., The molecular interaction parameter, $$P_n(R_m) = \frac{K_{mn}[L_n]}{\sum_j K_{mj}[L_j]}$$

provides a characterization of the molecular interaction between a binding agent, $R_m$, and an analyte, $L_n$, in the presence of analytes $\{L_j; 1 \leq j \leq N\}$, all of which exhibit a finite affinity, $K_{mj}$, for that binding agent. That is, $P_n$, $0 \leq P_n \leq 1$, represents a normalized specificity of binding agent $R_m$ for analyte $L_n$ in a multiconstitutent competitive reaction and serves as a robust characterization of that binding agent based on co-affinities displayed in a multiconstituent competitive reaction. See also P. H. von Hippel et al., Proc. Natl. Acad. Sci. USA 83, 1603 (1986), incorporated herein by reference.

The pattern of binding interaction of a analyte against a panel of binding agents may be used to characterize the analyte and compare it with other molecules. In addition, by generating the co-affinity matrix of a analyte using a reference panel of binding agents, such affinity may be used to determine if a sample later introduced to the panel of binding agents contains an impurity by observing the deviation in the binding pattern.

The present invention also provides use of superparamagnetic particles ("magnetic particles") as described in U.S. Pat. No. 5,759,820 and European Patent No. 83901406.5 (Sintef), which may then be used in integrated the sample preparation step with the assay step involving encoded bead arrays. Both of these references are incorporated herein by reference.

Superparamagnetic particles may be encoded with a chemically or physically distinguishable characteristic (e.g., flourescent tag) and used performing bioassays of the present invention. In certain embodiments, the particles are assembled using LEAPS, as with non-magnetic encoded beads. The encoded also be used in array generation, and assayed. The present invention also includes the formation of a planar array of encoded and functionalized superparamagnetic particles on a substrate by application of magnetic field to said particles.

Several methods for the synthesis of monodisperse superparamagnetic microspheres are known in the art. G. Helgesen et al., Phys. Rev. Lett. 61, 1736 (1988), for example, disclosed a method which utilizes porous and highly cross-linked polystyrene core particles whose interior surfaces are first nitrated, following which iron oxides are precipitated throughout the particle to produce a paramagnetic core. Following completion of this step, the particles are coated with functional polymers to provide a reactive shell. U.S. Pat. No. 5,395,688 to Wang et al. describes a process for producing magnetically responsive fluorescent polymer particles composed of a fluorescent polymer core particle that is evenly coated with a layer of magnetically responsive metal oxide. The method utilizes preformed fluorescent polymeric core particles which are mixed with an emulsion of styrene and magnetic metal oxide in water and polymerized. A two step reactive process such as this suffers from the drawback of possible inhibition of polymerization by the fluorescent dye or conversely bleaching of the fluorescence by the shell polymerization process.

The method also provides a novel process for making color encoded magnetic beads, a simple and flexible one-step process to introduce into preformed polymeric microparticles a well controlled amount of magnetic nanoparticles, prepared in accordance with the procedure described below, along with well controlled quantities of one or more fluorescent dyes. In an embodiment of the present invention, the quantity of the magnetic nanoparticles. is controlled to produce magnetic particles that form an array on a substrate upon application of magnetic field to said particles. This process involves swelling the polymer particles in an organic solvent containing dyes and magnetic nanoparticles and therefore applies to any polymer particle which can be subjected to standard swelling procedures such as those disclosed in the prior art of fluorescent staining of microparticles. Unlike encoding methods in which the magnetic material and the fluorescent dyes are each located to different areas of the (core/shell) of the magnetic particle, uniform swelling of particles ensures the distribution of magnetic particles throughout the interior volume. This process also permits the quantitative control of the nanoparticle as well as dye content over a wide range, thereby permitting the tailoring of the particles' magnetic susceptibility as well as fluorescence intensities. An additional method of the present invention to control the magnetic properties of the host particles, other than to control loading, is to tune the size of the magnetic nanoparticles by adjusting the water content of the micellar synthesis reaction (see below).

Physical or chemical coupling of biomolecules possible on the particle surface utilizing preexisting functional groups. Leaching out of magnetic nanoparticles is readily eliminated by growing a further polymeric shell on the particle.

In order that the invention described herein may be more fully understood, the following examples are set forth. It should be understood that these examples are for illustrative purposes and are not to be construed as limiting this invention in any manner.

EXAMPLES

Example 1

Optically Programmable Array Formation

Figure 9:
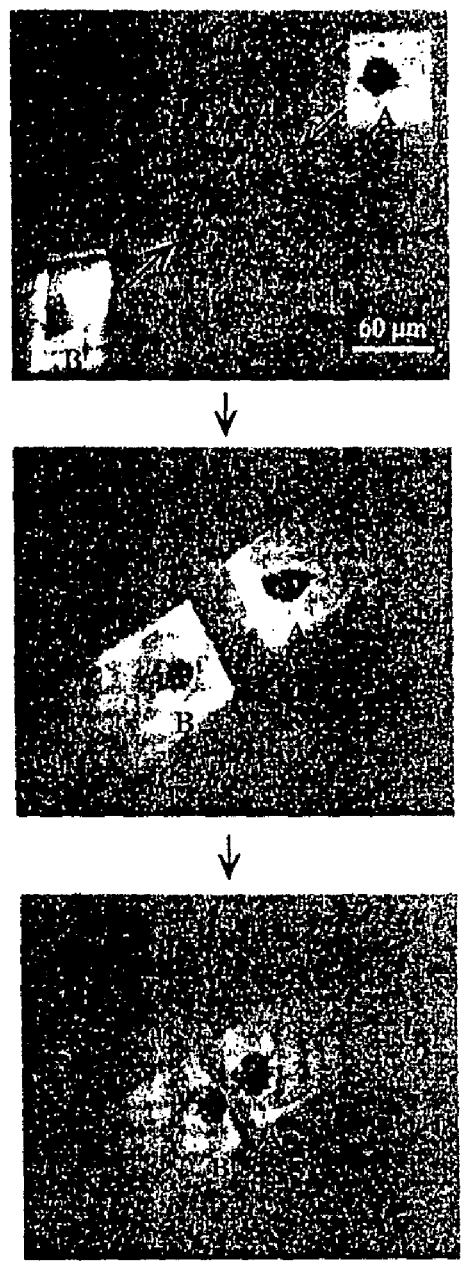
FIG. 9 is an illustration of optically programmable array assembly of random encoded arrays

As illustrated in FIG. 9, LEAPS serves to simultaneously assemble multiple random encoded subarrays and to "drag-and-drop" these subarrays into separate, but proximate locations on the chip within a common, enclosed liquid environment. Two sets of beads (2.8 μm Oligo-(dT)$_{25}$, Dynal, Oslo, Norway), dispensed from separate reservoirs A and B, were simultaneously assembled into distinct subarrays within the same fluid; sub-arrays were then simultaneously placed into desired destinations as directed by spatially varying illumination profiles which were generated and projected onto the substrate by a PC-programmable illumination pattern generator (described in U.S. Ser. No. 09/397,793, filed Sep. 17, 1999, which is incorporated herein by reference in its entirety). This drag-and-drop operation reduced the separation between the two sub-arrays from approximately 250 μm to 20 μm. Beads were moved at $5 V_{pp}$ at a frequency of 2 kHz; total power projected onto the substrate surface was ~5 mW. The combination of chemical and spatial encoding permits a given set of chemical bead markers to be used multiple times and reduces the demands placed on either encoding dimension while facilitating the realization of large coding capacities.

Example 2

Array Formation on Patterned Surface

Figure 10:
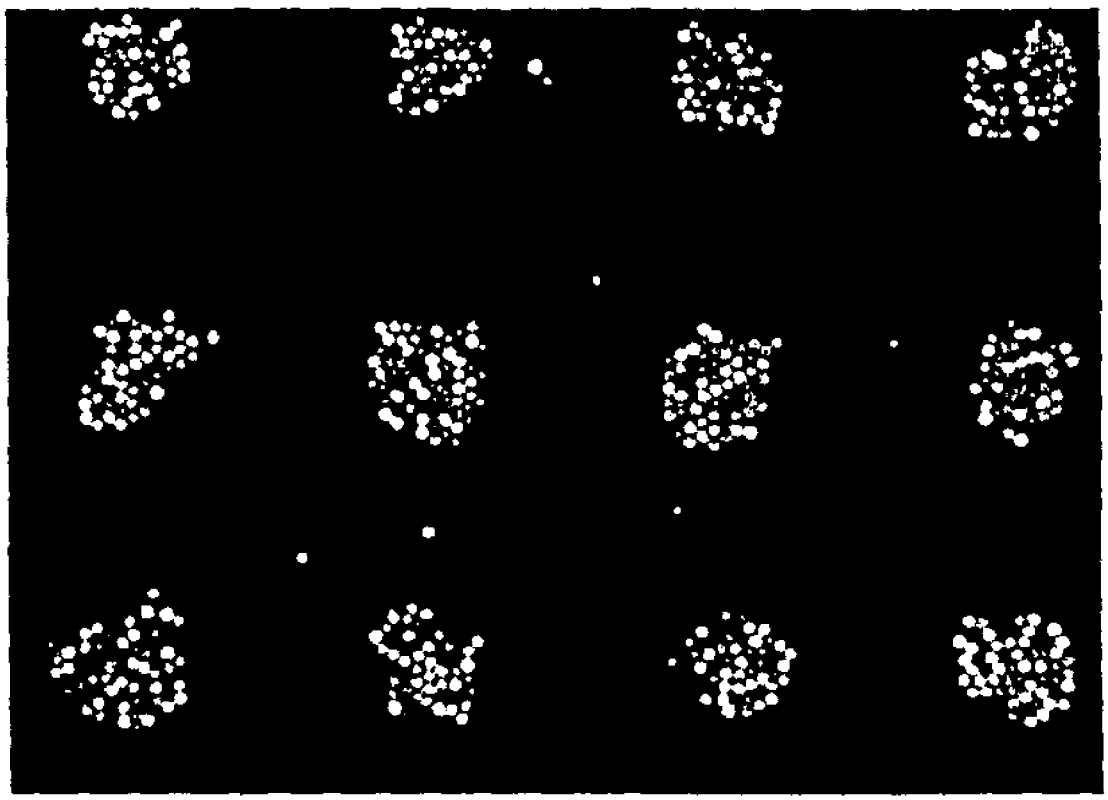
FIG. 10 is an illustration of an array composed of random encoded subarrays

Illustrated in FIG. 10 is an array of encoded beads assembled on a patterned silicon chip using an AC voltage of $1-2 V_{pp}$ and a frequency of 100-150 Hz, applied across a 100 μm electrode gap filled with an aqueous bead suspension; a thermal oxide (~1000 Å) on the substrate was patterned by etching the oxide to a thickness of 50-100 Å in a set of square features (~30×30 μm²) on 130 μm centers; arrays of similar layout also can be produced in response to suitable illumination patterns. Each sub-array shown here contains approximately 80 beads coupled with anti-cytokine monoclonal antibodies. Carboxylate-modified polystyrene beads of 5.5 μm diameter (Bangs Laboratory, Fishers, Ind.) were stained with a combination of two types of fluorescent dyes and were then functionalized with anti-cytokine-mAb. The assembly process ensures collection of all beads at the substrate surface. Bead encoding was as follows: IL-2 (Bright Red); IL-4 (Dim Red); IL-6 (Bright Green); M-CSF (Dim Green) and TNF-α (Yellow).

Example 3

Formation of Arrays of Magnetic Particles

Colloidal particles exhibiting a finite diamagnetic susceptibility, when disposed on a planar substrate can be assembled into ordered arrays in response to increasing magnetic fields. Commercially available superparamagnetic particles (Dynal, Oslo, NO), dispersed from a fluid suspension onto the planar surface of the lower of two parallel bounding surfaces of a fluid cell ("sandwich" geometry), when exposed to a homogeneous axial magnetic field (oriented normal to the substrate plane), will form ordered assemblies. As a function of increasing magnetic field strength, and for given diamagnetic susceptibility of the particles as controlled by the manufacturing process known to the art, ordered planar assemblies and linear strings of beads oriented normal to the substrate can be formed. Permanent magnets can be designed so as to produce the field strength required to realize the desired configuration of the assembly. Requisite magnetic field configurations can be produced by an electromagnet in solenoid or Helmholtz configuration known to the art; the substrate can be introduced into the magnet bore or can be placed in immediate proximity to the coil(s) outside of the bore so as to ensure the orientation of the field substantially normal to the substrate plane. Spatially modulated magnetic fields can be produced by patterning the substrate with permalloy using methods known to the art.

Example 4

Formation of Random Bead Assemblies

Aliquots of solution containing suspended beads were placed onto several distinct positions on a planer substrate of silicon capped with a thin silicon oxide layer (other substrates may be used here). Beads were allowed to settle under gravity to form random assemblies. To delineate discrete positions on the substrate, one of the following two methods were used. According to the first method, a silicon gasket (of 250 um thickness), displaying a grid of multiple round holes of 1 mm or 2 mm diameter (Grace Bio-labs, Bend, Oreg.) is placed on the hydrophillic surface to define microwells (of 0.25 to 0.5 ul volume) for multiple discrete samples of bead suspension. According to the second method, small aliquots of fluid containing beads (0.2 ul to 0.5 ul in volume) are directly placed onto a hydrophillic surface in one or more designated areas so as to ensure formation of discrete droplets; spacers are not needed in this case. As solvent evaporates (at room temperature or, for rapid drying, at elevated temperature (about 60 C), beads are left in random positions on the substrate. DNA polymorphism reactions have been tested in assemblies formed in both manners. Optionally, beads settling under gravity may be immobilized by chemical capture layers provided on the substrate. An application of random bead assemblies to determine affinity constants in a multiplexed format is described in Example 6.

Example 5

An Automated Chip-scale Array Manufacturing Process

Figure 11:
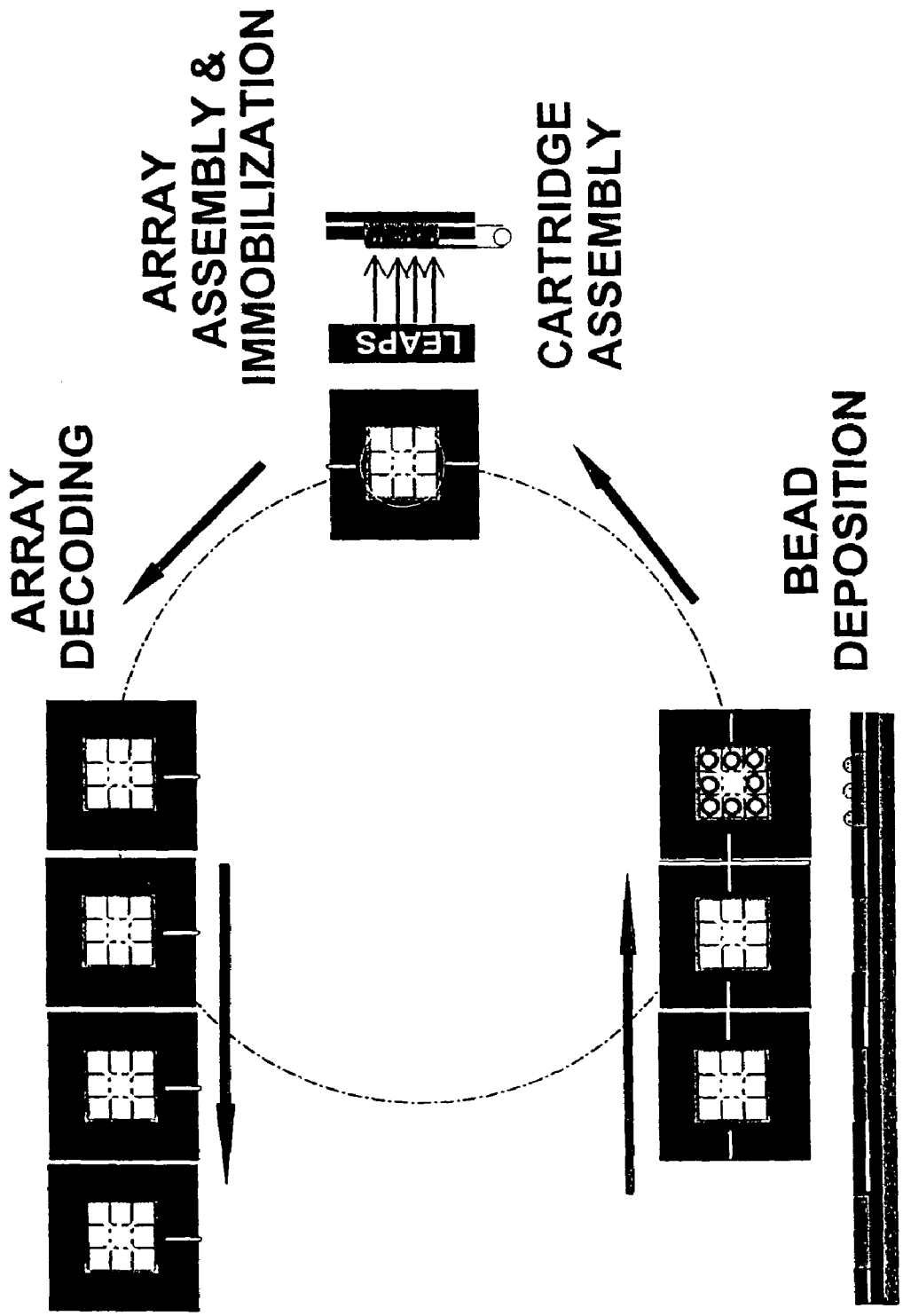
FIG. 11 is an illustration of stations in an automated chip-scale bead array manufacturing and QC process

As illustrated in FIG. 11, the process involves liquid handling and pipetting of beads onto chips mounted in single-chip cartridges or multi-chip cartridges. Bead arrays are formed using methods such as those in Examples 1, 2 or 3., followed by array immobilization and decoding. The resulting decoding images are stored for later use along with an optional chip ID ("bar code").

Example 6

Determination of Affinity Constants by Post-assay Analysis of Bead Assemblies

Quantitative binding curves for the cytokines TNF-α and IL-6. Binding curves were generated by performing sandwich immunoassays using chemically encoded beads in suspension, said suspensions being confined to one or more reaction compartments delineated on-chip, or in one or more reaction compartments off chip. By completing the reaction with beads maintained in suspension, assay kinetics similar to homogeneous assays can be attained. Following completion of the binding reaction, beads were assembled on chip to permit multiplexed quantitative image analysis. Random assemblies prepared according to Example 4 or ordered bead arrays prepared according to Example 1 or 2 may be used. An advantage of ordered, dense assemblies produced by the methods of Examples 1 or 2 is the higher spatial density and higher assay throughput attained by processing a greater number of beads.

Figure 12:
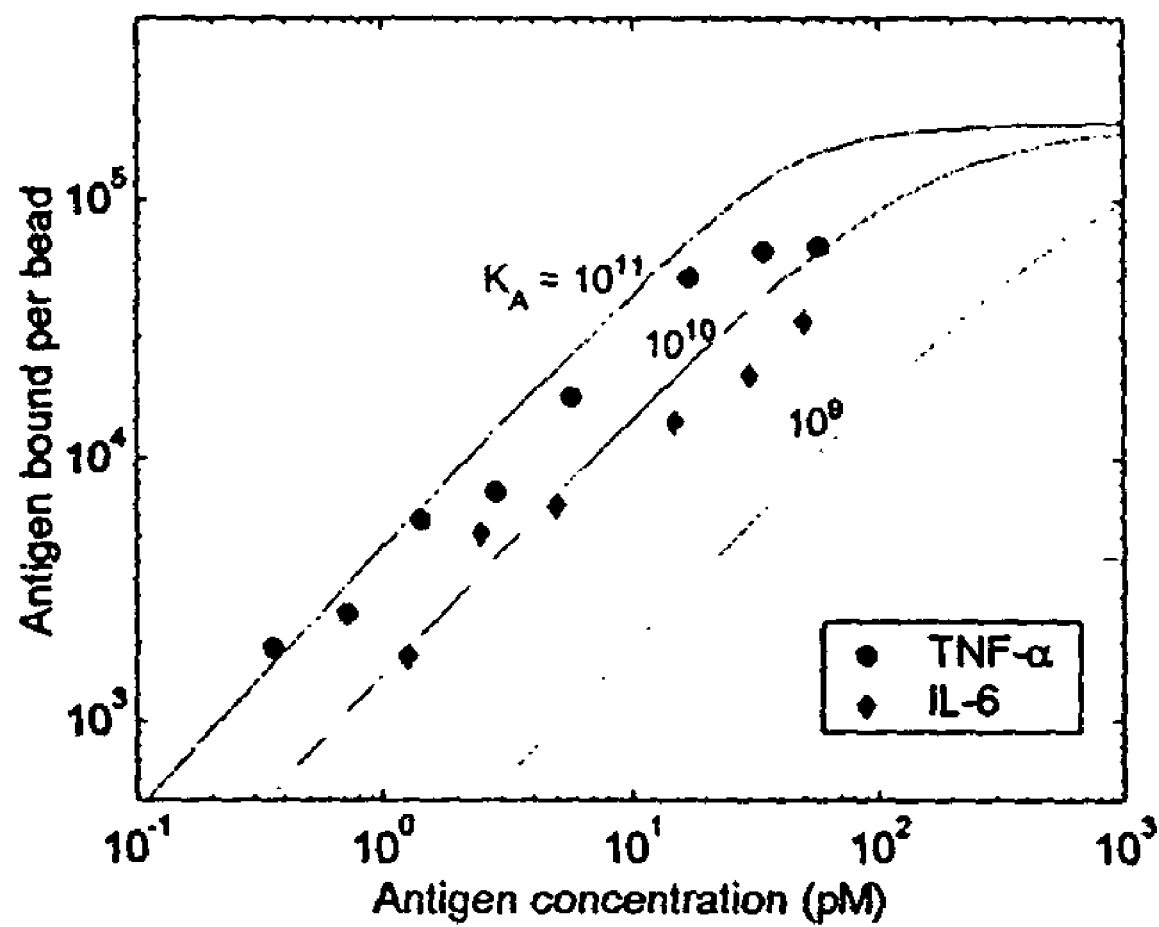
FIG. 12 is an illustration of quantitative binding curves for two cytokines

As an illustration, FIG. 12 displays quantitative binding curves for TNF-α and IL-6, obtained from randomly dispersed beads. A commercial-grade 8-bit video-CCD camera (Cohu, San Diego, Calif.) was used in a mode permitting multi-frame integration. The range of concentrations of antigen used in the two assays was 700 fM to 50 pM for TNF-α and 2 pM to 50 pM for IL-6. At each concentration, the number of molecules bound per bead was estimated by comparison with calibration beads coated with known quantities of Cy5.5-labeled BSA per bead; requisite adjustments were made to account for differences in fluorescence quantum efficiency between labeled secondary antibodies and BSA.

This format of analysis permits the determination of the affinity constant, $K_A=[LR]/([R_0-LR][L])$, where, in accordance with the law of mass action, [LR] denotes the number of receptor-ligand pairs per bead and [L] denotes the solution concentration of ligand. By specifying the number of beads per ml, $n_B$, and specifying a value for $[R_0]$ in terms of the number of receptors per bead, theoretical binding curves, computed for given $K_A$, are compared to a plot of the number of bound molecules per bead as a function of bulk ligand concentration. The absolute number of ligands bound per bead may be determined for given bulk concentration by measuring the mean fluorescence intensity per bead and referencing this to the fluorescence intensity recorded from calibration beads included in the array.

The estimated number of molecules bound per bead is compared to theoretical binding curves derived from the law of mass action. The three curves shown correspond to values of the affinity constant, $K_A$, of $10^{11}$/molar, $10^{10}$/molar and $10^9$/molar, respectively. The initial number of antibodies per bead, $R_0$, equals $2 \times 10^5$/bead and $n_B=10^5$/ml. Each data point represents the average of three replicates, with an assay-to-assay variation of <45%. Setting the assay sensitivity to correspond to that level of fluorescence which yields a signal-to-noise level of unity in the assay images, the sensitivity of the cytokine assays characterized in FIG. 12 is set at ~2,000 bound ligands/bead, corresponding to respective detected concentrations of 700 fM for TNF-α and 2 pM for IL-6.

While commercial ELISA kits use enzymatic amplification to enhance sensitivity, at the expense of additional complexity relating to assay conditions and controls, our bead array assay format, even without enzymatic amplification, our on-chip assay format permits monitoring of cytokines at circulating levels (Normal TNF-α level in serum is 50-280 fM and normal IL-6 level in serum is 0-750 fM. www.apbiotech.com/technical/technical_index.html), providing a dynamic range which approaches that of standard, i.e. amplified single-analyte ELISA assays (Assay kits of R & D Systems and Amersham (not the recent High-Sensitivity assays). Further improvements at hardware and software levels are possible.

Example 7

Genotyping by Polymorphism Analysis

Figure 13:
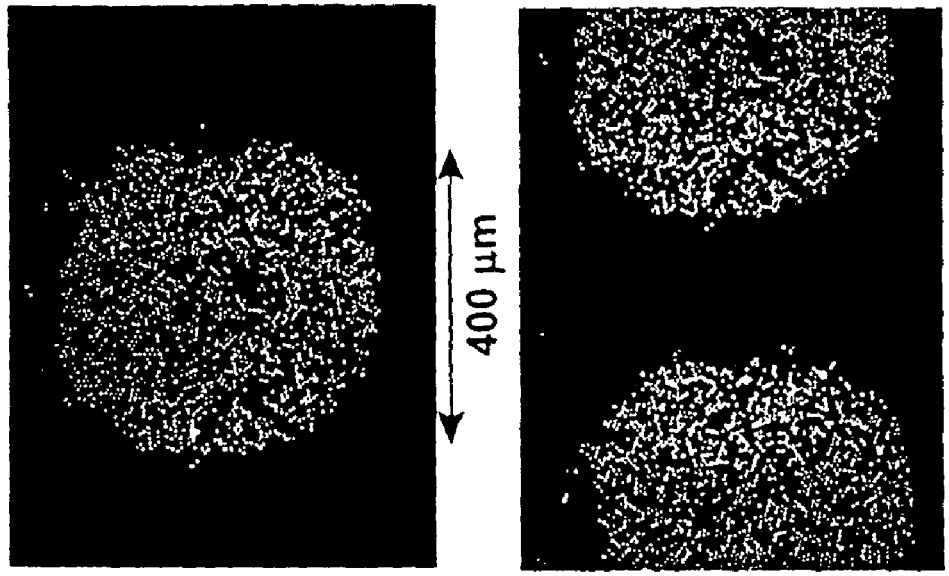
FIG. 13 is an illustration of array design for polymorphism analysis
Figure 13:
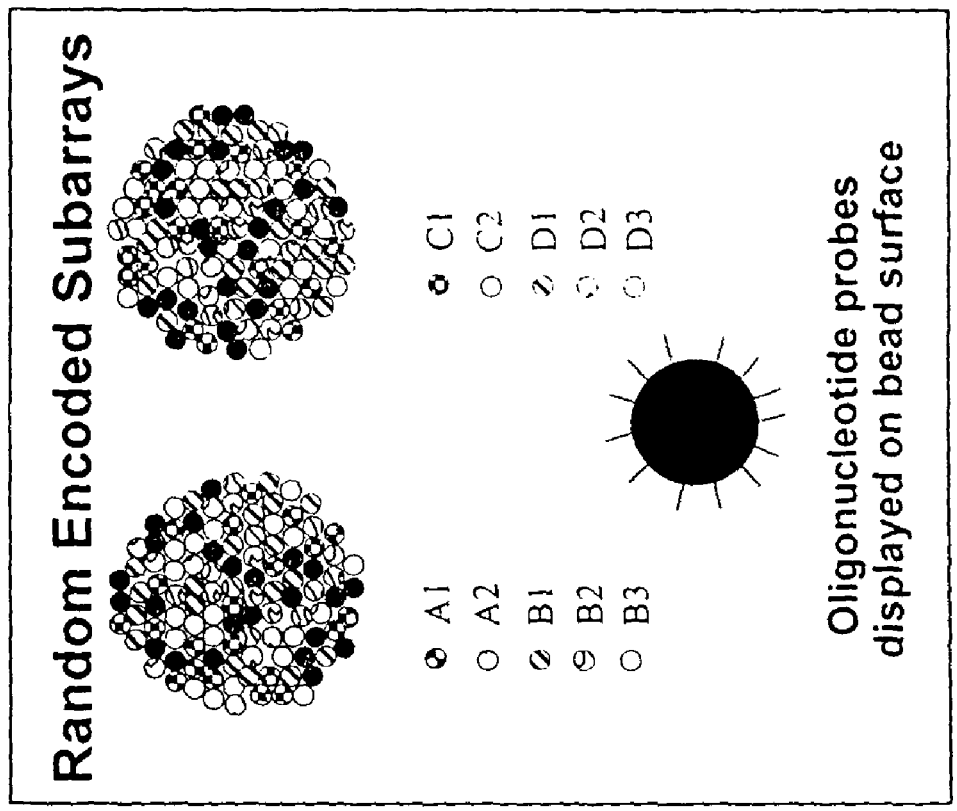

To illustrate the application of the present invention to the implementation of genotyping, FIG. 13 shows the design of the assay in which five pairs of 20-mer binding agents corresponding to four polymorphic regions of a gene were coupled to color-encoded beads. The pairs of binding agents α1, α2 and β1, β2 each display a single nucleotide difference in their respective sequences; the pair δ3, δ4 displays a difference of three nucleotides, the binding agents in the set γ1, γ3, γ3, γ4 display small insertions and deletions. The ten binding agents were are divided into two subgroups of five which were incorporated into two subarrays. In this example, there are several hundred beads for each type. Following bead immobilization, an on-chip hybridization reaction was performed in TMAC buffer (2.25 M tetramethylammonium chloride, 37 mM Tris pH 8.0, 3 mM EDTA pH 8.0, and 0.15% SDS) at 55° C. for 30 min. The analyte is a 254-base PCR fragment produced from a patient sample and fluorescently labeled at the 5'-prime end with BODIPY 630/650 (Molecular Probes, Eugene, Oreg.). Image acquisition was performed after replacing the assay buffer with fresh TMAC buffer.

Figure 14:
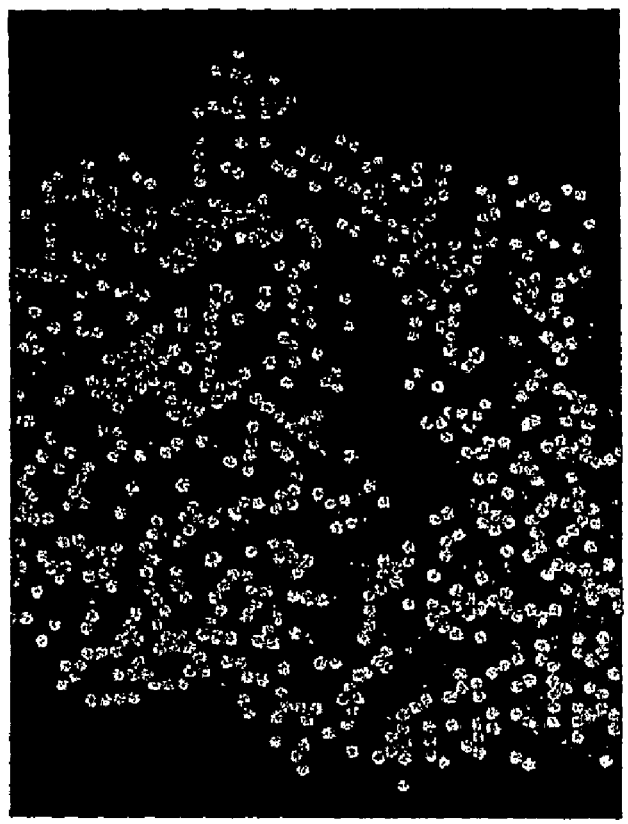
FIG. 14 is a fluorescence micrograph of assay and decoding images recorded from one subarray shown in FIG. 13 in the course of polymorphism analysis
Figure 14:
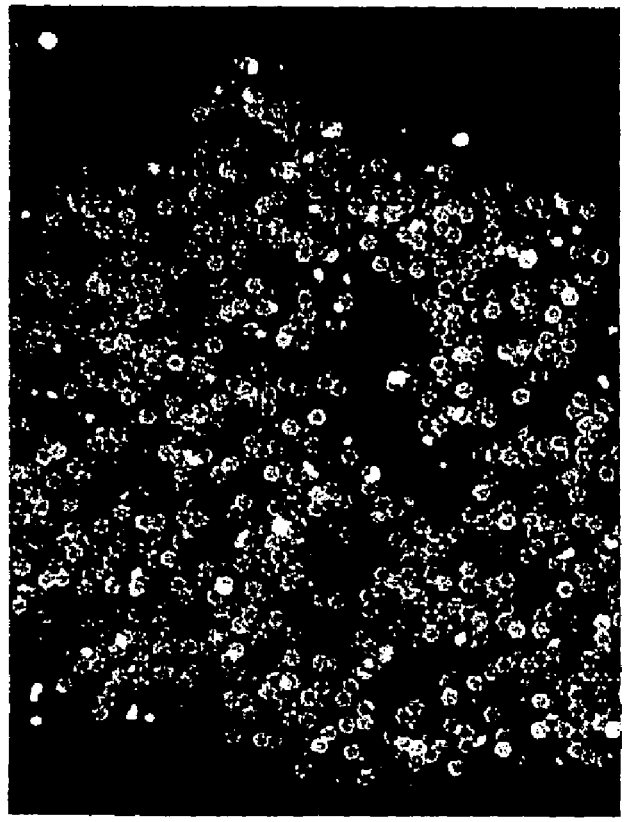
Figure 15:
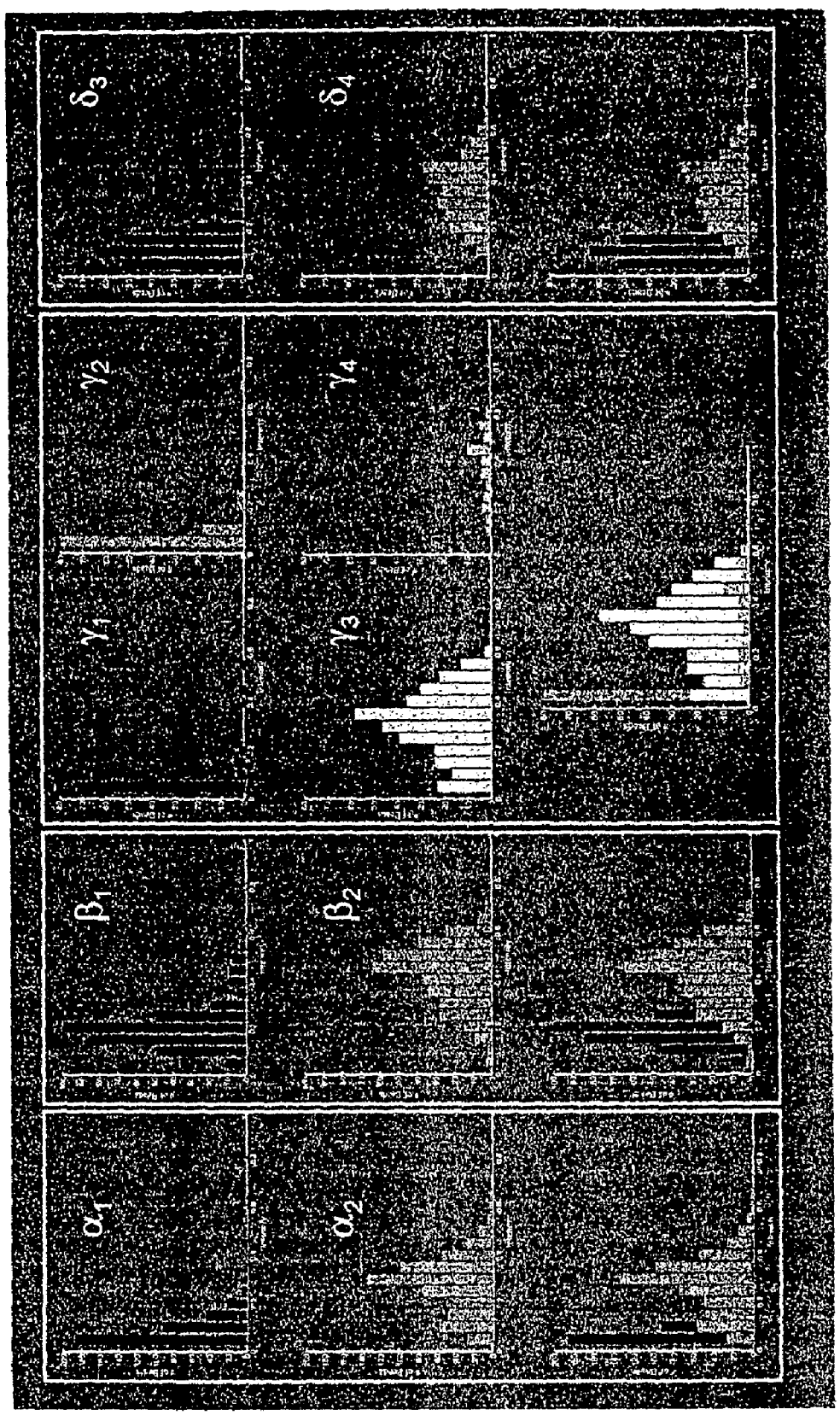
FIG. 15 is an illustration of assay results in the form of intensity histograms obtained from the analysis of assay images such as the one illustrated in FIG. 14.

FIG. 14 shows decoding and assay images for one subarray. Each bead shown in the assay image obtained after hybridization is analyzed to determine fluorescence intensity and bead type; as with the cytokine assay, the latter operation compares assay and decoding images using a template matching algorithm. FIG. 15 displays the resulting intensity histograms for each bead type: in these histogram plots, the horizontal axis refers to relative signal intensity from 0 to 1 and the vertical axises refer to bead numbers. The histograms show that most of the beads displaying probe α1 bind no analyte while most of the beads displaying probe α2 exhibit significant binding; the mean signal level of α2-beads exceeds that of α2-beads by a factor of ~3.2, indicating that analyte contains DNA sequences complementary to α2 but not α1. For the patient sample presented here, the histogram indicates a genotype of the analyte DNA characterized by complementarity to binding agents α2, α2, γ3, γ4 and δ4 in the polymorphic region of the gene.

Example 8

Gene Expression Analysis: cDNA Fragments

The method of the present invention has been used to fabricate arrays composed of beads displaying oligonucleotides as well as DNA fragments (e.g., up to 1,000 bases in length). Strands were biotinylated at multiple positions by nick-translation and were attached to streptavidin-functionalized beads (M-280, Dynal, Oslo, NO). Arrays were formed using an AC voltage of 800 Hz at $10V_{pp}$.

Example 9

Looped Probe Design for Universal Labeling

Figure 16:
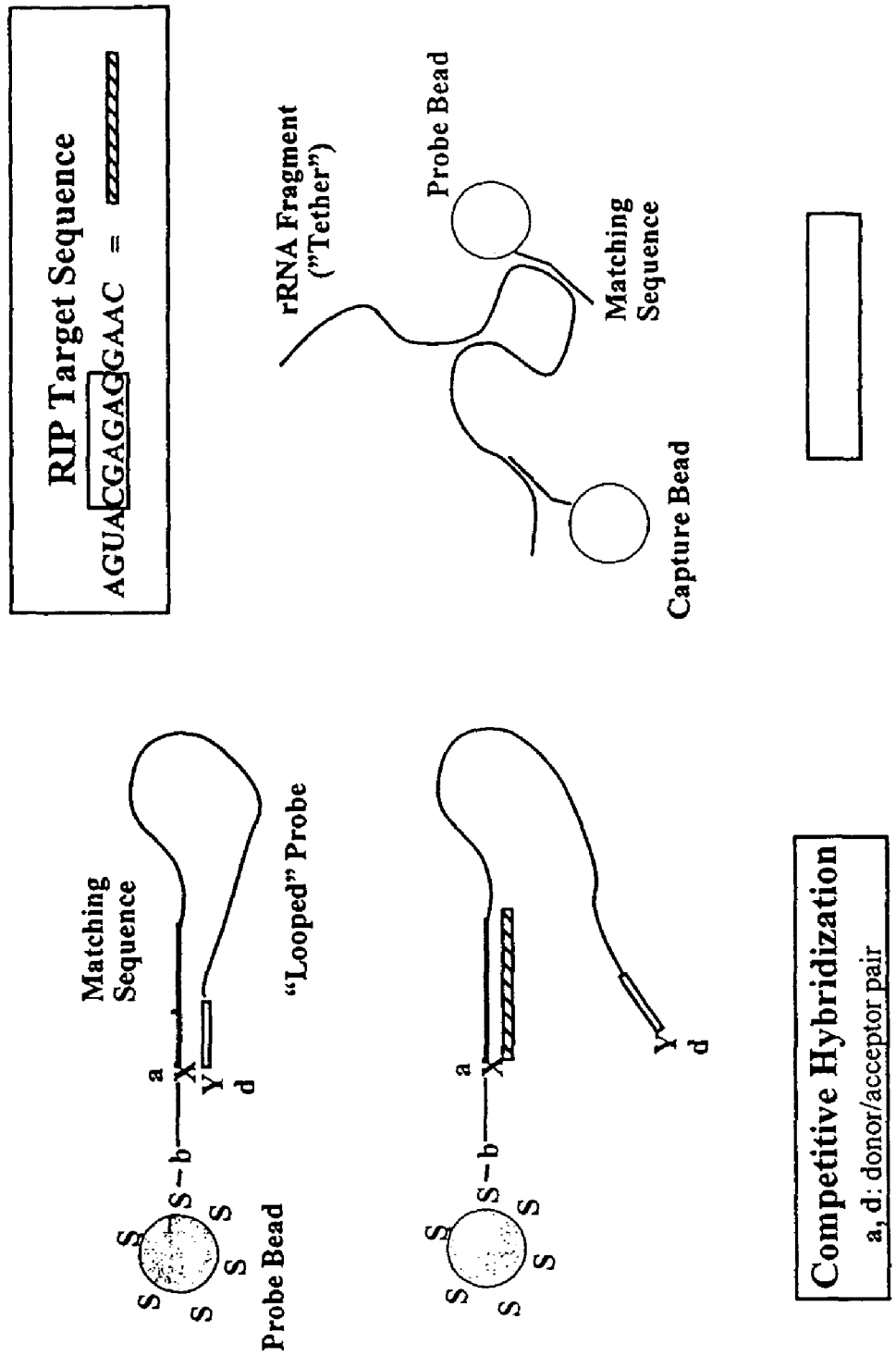
FIG. 16 is an illustration of design of a "looped probe" for hybridization assays

A looped probe design in FIG. 16 takes advantage of fluorescence energy transfer to obviate the need for labeled target. As with the molecular beacon design (S. Tyagi, D. P. Bratu. F. R. Kramer, *Nature Biotech.* 16, 49-53 (1998)), the probe in FIG. 16 assumes two different states of fluorescence in the closed loop and open loop configurations, but in contrast to the molecular beacon contains a portion of its binding motif within the stem structure to permit molecular control of stringency in competitive hybridization assays.

Example 10

Quantitative Multiplexed Profiling of Cytokine Expression

Figure 17:
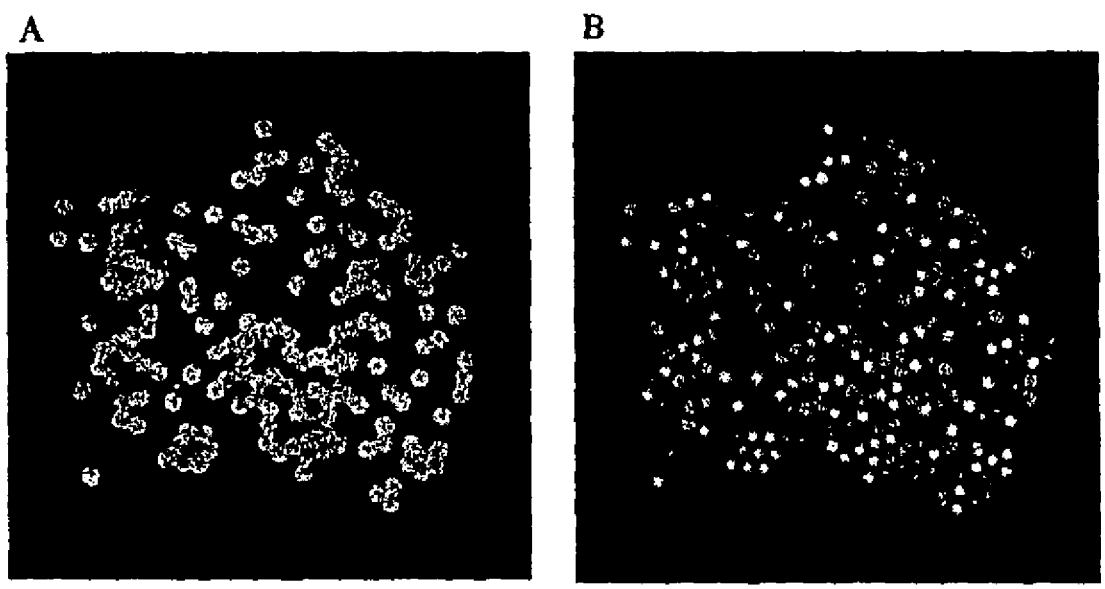
FIGS. 17A and 17B are fluorescence micrographs of assay and decoding images recorded in the course of the analysis of multiple cytokines

FIG. 17 displays a pair of assay and decoding images recorded from a single random array in a multiplexed sandwich immunoassay. An array containing five distinct types of beads, each displaying a monoclonal anti-cytokine antibody (mAb), was exposed to a sample solution (such as serum) containing two cytokine antigens (Ag). Subsequent addition of Cy5.5-labeled secondary antibodies (pAb*) results in the formation of ternary complexes, mAb-Ag-pAb*. The on-chip immunoassay was performed by adding 300 µl of sample with 7 nM cytokines in assay buffer (20 mM NaPi pH 7.4, 150 mM NaCl, 10 mg/ml BSA) to the bead array immobilized on the chip, and allowing the reaction to proceed at 37° C. for one hour. The buffer was replaced by adding 12 nM solution of labeled secondary antibodies in assay buffer. After one hour of incubation at 37° C., fresh buffer was added on top of the chip and image acquisition was performed. Antibodies and antigens used in the assays were obtained from R&D Systems (Minneapolis, Minn.); the secondary antibody was labeled with Cy5.5 using a standard kit (Amersham Pharmacia Biotech, Piscataway, N.J.).

The decoding image FIG. 17B shows five types of beads in a false-color display with the same encoding pattern as that of FIG. 10. All beads are of the same size (5.5 µm diameter); the apparent difference in the size of beads of different types in the decoding image is an artifact reflecting different internal bead staining levels and "blooming" during CCD recording of the decoding image. Comparison (using the image analysis methods disclosed herein) of the decoding image with the assay image in FIG. 14A reveals that active beads, of yellow and bright green types, captured TNF-α and IL-6, respectively. This assay protocol has been extended to the following set of twelve cytokines: IL-1α, IL-1β, IL-2, IL-4, IL-6, TGF-β1, IL-β2, EGF, GM-CSF, M-CSF, MCP-1 and TNF-α. The on-chip immunoassay requires no additional washing other than changing reagent solutions between assay steps. Comparison between assay and decoding images shows that two different cytokines were present in the sample, namely IL-6 and TNF-α. The pre-formed arrays described in this example also permit the determination of affinity constants in a manner analogous to the analysis described in Example 6.

Example 11

Aptamers for Protein Profiling

Aptamers may be selected from large combinatorial libraries for their high binding affinities to serum proteins (L. Gold, B. Polisky, O. Uhlenbeck, M. Yarus, *Annu. Rev. Biochem.* 64: 763-797. (1995)). Random encoded arrays of aptamer-functionalized beads would serve to monitor levels of serum proteins; correlations in binding patterns on the array (see also Example 10) may serve as a phenotype of disease states.

Example 12

Mixed DNA-Protein Arrays

Of significant interest to genomic functional analysis is the fact that the method of the present invention accommodates protein and DNA arrays without change in array manufacturing methodology. Specifically, mixed arrays composed of beads displaying DNA and corresponding proteins can be used to analyze the gene and gene product within the same fluid sample.

This has been demonstrated for a combination of immunoassay and DNA hybridization. For example, a mixed array composed of beads functionalized with anti-cytokine monoclonal antibodies (mAb) and with oligonucleotides was produced. Two sequential assays were performed on this single chip. First, an immunoassay was performed in accordance with the protocol described in Example 10. Following completion of the on-chip immunoassay, image is acquired and the DNA analyte was added to the hybridization buffer (2×SSC, 1×Denhardt's) at a final concentration of 20 nM and allowed to react at 37° C. for 1 hr. Fresh hybridization buffer was added to the chip and image acquisition was performed to record of the additional hybridization assay.

Example 13

Affinity Fingerprinting

The analysis of receptor-ligand interactions relevant to prior art methods assumes ideal specificity. That is, only the ideal situation is considered of a single ligand present in solution reacting with its matching receptor and vice versa. However, in most multiple assay systems, a considerable level of cross-reactivity may exist. That is, any single ligand may associate with several receptors, while any single type of receptor may have a finite affinity towards more than one ligand.

The present invention includes a model that is developed to analyze multiplexed READ assays for such a system under the following assumptions: each of these reversible reactions is characterized by its own affinity constant; no reaction occurs between the bulk species; there is no interaction between the complexes formed on the surface. These assumptions can be relaxed, at the expense of increasing the complexity of modeling, by accounting for reactions in the bulk and between the surface species. The standard reaction-diffusion equation for single receptor-ligand pair formation [R. W. Glaser, Anal. Biochem. 213, 152-161 (1993)], is generalized to allow for multiple reactions at each bead surface:

$$\frac{\partial [L_i \cdot R_j]}{\partial t} = k_{on,ij}[L_i]\left([R_{j,0}] - \sum_{n,m}[L_m \cdot R_n]\right) - k_{off,ij}[L_i \cdot R_j] \quad \forall\, i, \quad (2)$$

$$j, L_i \equiv L_i(t, x, 0)$$

The first term on the right of Eq. (1) describes the association of ligands and receptors into complexes and involves of concentration of free sites on the surface. The second term describes the disassociation of complexes by way of release of ligands, thereby freeing up receptor sites for further reaction. Since a maximum of (i×j) bimolecular complexes can form, there could be as many boundary conditions generated from the above equation. For the equilibrium case, the left hand-side of Eq. (1) is set to zero, and the matrix of coaffinities, $[K_{ij}]=k_{on,ij}/k_{off,ij}$, can then be defined to accommodate cross-reactivities between multiple species in the bulk and on the surface. In a batch reactor under equilibrium conditions, we may solve the system of differential equations to obtain the number of molecules of each ligand bound on beads of each type.

| | | |
|---|---|---|
| $L_1$ | Ligand concentration | 10 pM |
| $L_2$ | Ligand concentration | 100 pM |
| $R_{01}$ | Initial receptor concentration | $1 \times 10^4$/bead |
| $R_{02}$ | Initial receptor concentration | $1 \times 10^4$/bead |
| $n_{B1}$ | Bead number density | $1 \times 10^4$/ml |
| $n_{B2}$ | Bead number density | $1 \times 10^4$/ml |
| $[K]$ | Coaffinity matrix | $[1 \times 10^{11}\ 1 \times 10^9$ $1 \times 10^8\ 1 \times 10^{11}]$ 1/mole |

As an illustrative example, the ligand distribution has been calculated (from the model in Eq (1)) for a reference set of two ligands and two types of receptors immobilized on two different sets of beads. The coaffinity matrix is assumed known for each ligand-detection combination in the reference set; to investigate the detection of a third ligand, it is assumed here that diagonal elements of the 2×2 matrix, $[K_{ij}]$, are large compared to off-diagonal elements. The presence of a third ligand in the reactor alongside the two original ligands perturbs the equilibria between the various complexes and the reactants in the reference system, and for ligand molecules tagged with fluorescent labels, the intensity observed from the perturbed system differs from that observed in the reference case.

Figure 18A:
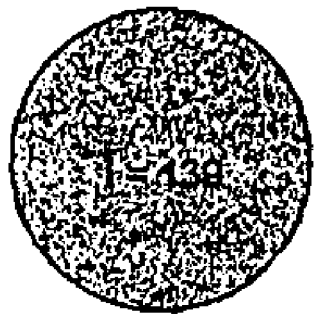
FIGS. 18A and 18B are illustrations of numerical simulations of cross-correlations in receptor-ligand systems with multiple competing receptor-ligand interactions
Figure 18A:
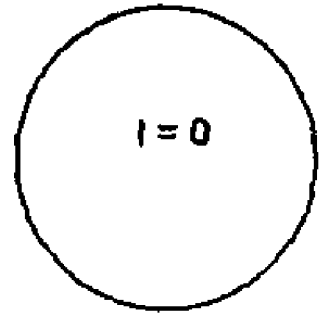
Figure 18A:
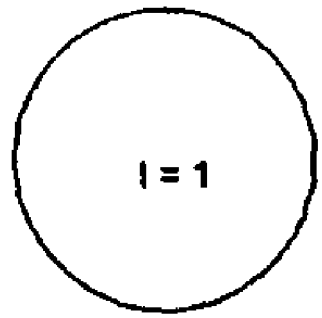
Figure 18A:
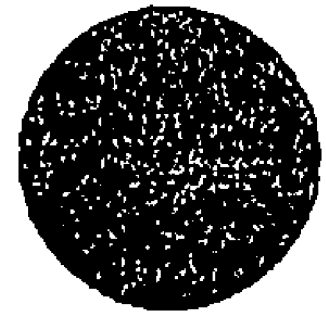
Figure 18B:
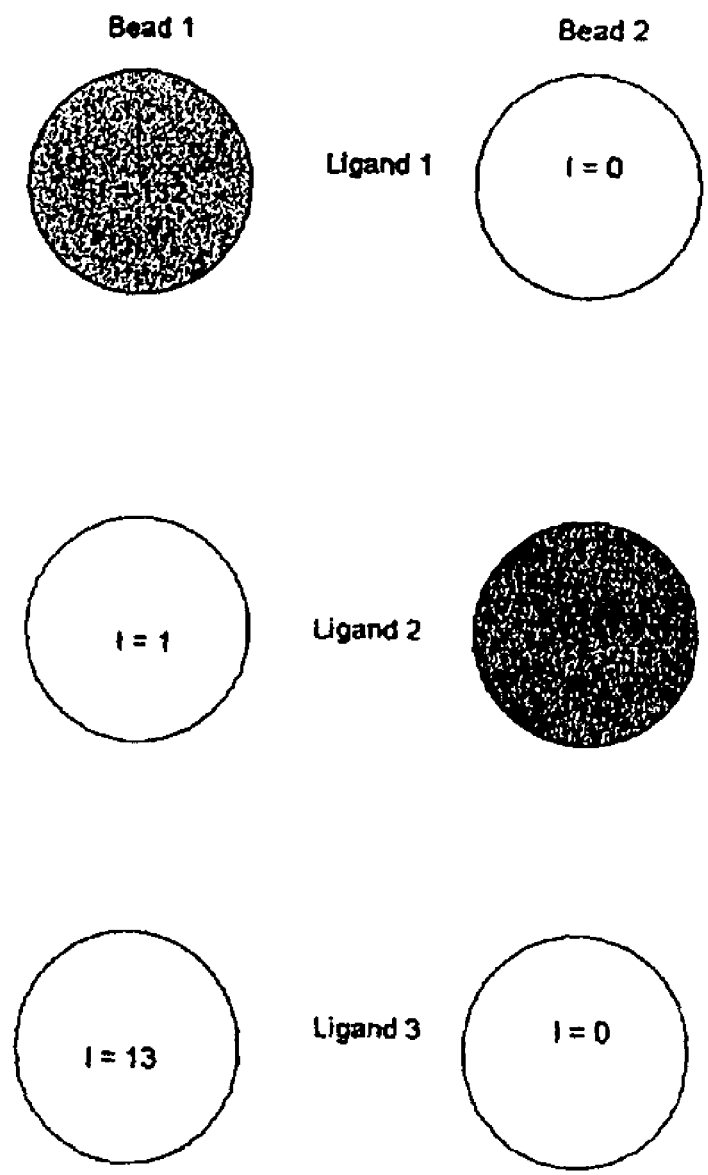

FIG. 18A shows the reference case in which the concentrations and coaffinity matrix were set to the values shown in the accompanying table; the bead intensity was defined on a linear scale of 0-255, the latter representing the intensity of the brightest beads. FIG. 18A shows the contribution of each ligand to the bead intensity. Due to the lower concentration of $L_1$, the intensity of Bead 1 is less compared to Bead 2, cross-reactivities are essentially undetectable.

Next, the system was perturbed with a third ligand, taking the concentration $L_3$ to be 1 pM and assuming that the new ligand has considerable amount of cross-reactivity with each of the receptors; $K_{3,1}=1\times10^{11}/M$, $K_{3,2}=1\times10^{10}/M$. Calculation of the fluorescent intensity of each bead in the presence of the third ligand yields the pattern in FIG. 18A which reveals an increase in the intensity of Bead 1 due to the third ligand, while leaving the intensity of Bead 2 unaffected due to the higher concentration of $L_2$ in the system and the lower affinity of $L_3$ to $R_2$. Thus, $L_3$ may be detected under the condition that it has a relatively high affinity to one of the receptors and is in significant amount compared to the competing ligand.

The evaluation of the coaffinity matrix (and comparison with theoretical modeling as disclosed herein) under conditions in which a mixture of ligands is permitted to interact with a multiplicity of receptors arranged in a random encoded bead array format provides a methodology to establish a characteristic feature set of cross-correlations in the mutual competitive binding affinities of multiple ligands and receptors. These co-affinities provide a robust means to characterize receptor-ligand binding equilibria by their affinity fingerprinting patterns. Deviations from well-defined reference cases also permit detection of "perturbing" ligands in solutions.

Example 14

Multiplexed Analysis of Reaction Kinetics

As illustrated in the foregoing examples, extensive washing generally is not required to discriminate beads from a background of solution fluorescence. Consequently, assay image sequences may be recorded in a homogeneous assay format to document the evolution of a binding reaction and to determine kinetic data for each of the binding reactions occurring.

Homogeneous binding assays may be performed in simple "sandwich" fluidic cartridges permitting optical microscopic imaging of the bead array and permitting the introduction of an analyte solution into a chamber containing a random encoded array of beads. More generally, the array also may be exposed to an analyte or other reaction mixtures under conditions of controlled injection of fluid aliquots or continuous flow of reactants or buffer. Using theoretical modeling, optimal combinations of relevant performance control parameters of this bead array reactor may be identified to minimize the time to equilibration or to maximize the portion of analyte captured by the array [K. Podual and M. Seul, TM KP-99/02]. Flow rate can be controlled by any of a number of available pumping mechanisms [M. Freemantle, C&EN, 77: 27-36].

TABLE

List of parameters used in simulations (FIG. 18)

| Parameter, units | Value |
| --- | --- |
| Initial Receptor Coverage $c_{R,0}$, moles/m² | $8 \times 10^{-9}$ |
| Vol Flow Rate, Q, µl/s | 1.0 |
| Diffusivity, D, cm²/s | $1 \times 10^{-7}$ |
| ON-Rate, $k_{on}$, /(M s) | $1 \times 10^{5}$ |
| Affinity Constant, $K_A$, /M | $1 \times 10^{11}$ |
| "Sandwich" Reactor Gap Size H, mm | 0.1 |
| Reactor Length, L, mm | 10 |
| Reactor Width, W, mm | 10 |

Figure 19:
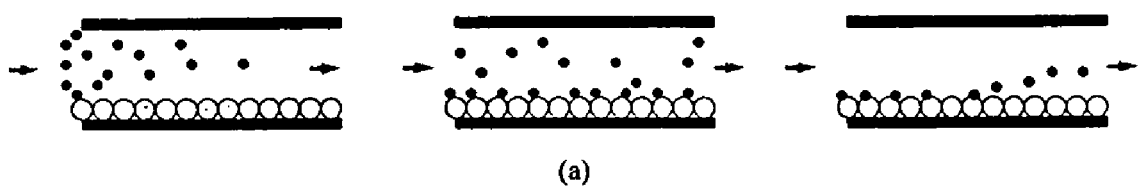
FIG. 19 is an illustration of numerical simulations of receptor-ligand association and disassociation kinetics
Figure 19:
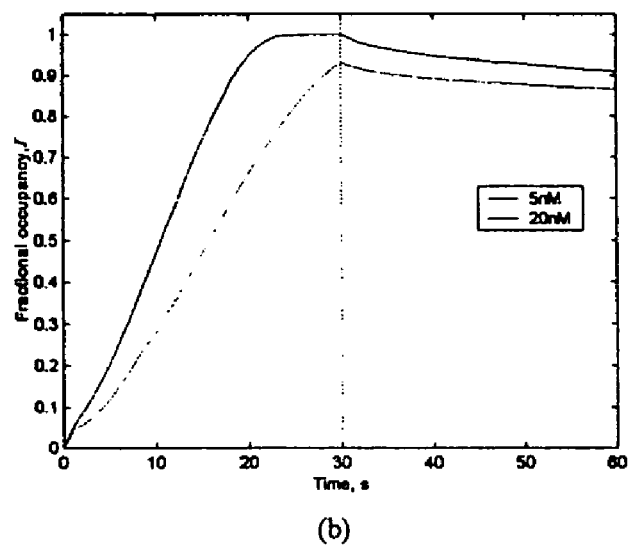

The analysis of image sequences permits kinetic data to be generated from which ON-rates and OFF-rates are determined with the aid of a theoretical model of the reaction-diffusion kinetics of the type illustrated in the foregoing example in FIG. 19. FIG. 19A displays stages in an adsorption-desorption cycle involving solution-borne analytes and a bead array immobilized at the bottom of a "sandwich" reaction chamber. The first panel depicts the initiation of the adsorption process; the second panel depicts the state of the reactor close to equilibrium when most of the beads have reached equilibrium; the last panel depicts the state of the reactor under the desorption cycle in which ligand-free fluid is injected and adsorbed molecules desorb from the bead surface. FIG. 19B displays the adsorption-desorption kinetics of a single receptor-single ligand system obtained by numerical solution of a reaction-diffusion system for a single type of receptor-ligand reaction; two cases of different concentrations of ligand are shown. Parameters used in the simulation are listed in the accompanying Table.

In contrast to prior art methods [D. G. Myszka, Curr. Opin. Biotechnol. 8: 50-57.], the present method relies on imaging and permits multiplexing. In addition, generalized models of the type introduced in Example 6 permit the analysis of complex binding kinetics for multiple simultaneous receptor-ligand interactions even in the presence of cross-reactions between multiple ligands and receptors.

The ability to monitor reaction kinetics in an array format will enable several approaches to enhancing the specificity of receptor-ligand or binding agent-analyte interactions in complex mixtures. For example, temperature programming may be invoked to enhance the specificity of DNA hybridization reactions. Similarly, the stringency of conditions applied to a hybridization reaction may be varied while the array response is being monitored; for example, hybridization may be conducted in a hybridization buffer under conditions leading to excess "non-specific" binding; specificity is enhanced by switching to a wash buffer of increasing stringency while monitoring the array response.

Example 15

Multi-Step Assay Sequences Using Encoded Arrays of Magnetic Particles

Methods and apparatus using biochemically functionalized super-paramagnetic particles for sample preparation in molecular and cellular biology and for a variety of enzyme-catalyzed on-bead reactions have been described ["Biomagnetic Techniques in Molecular Biology", Technical Handbook, 3rd Edition, 1998, Dynal, Oslo, NO]. These bead-based methods can be combined with the Random Encoded Array Detection format of the present invention to implement multi-step on-chip assay manipulations.

Figure 20:
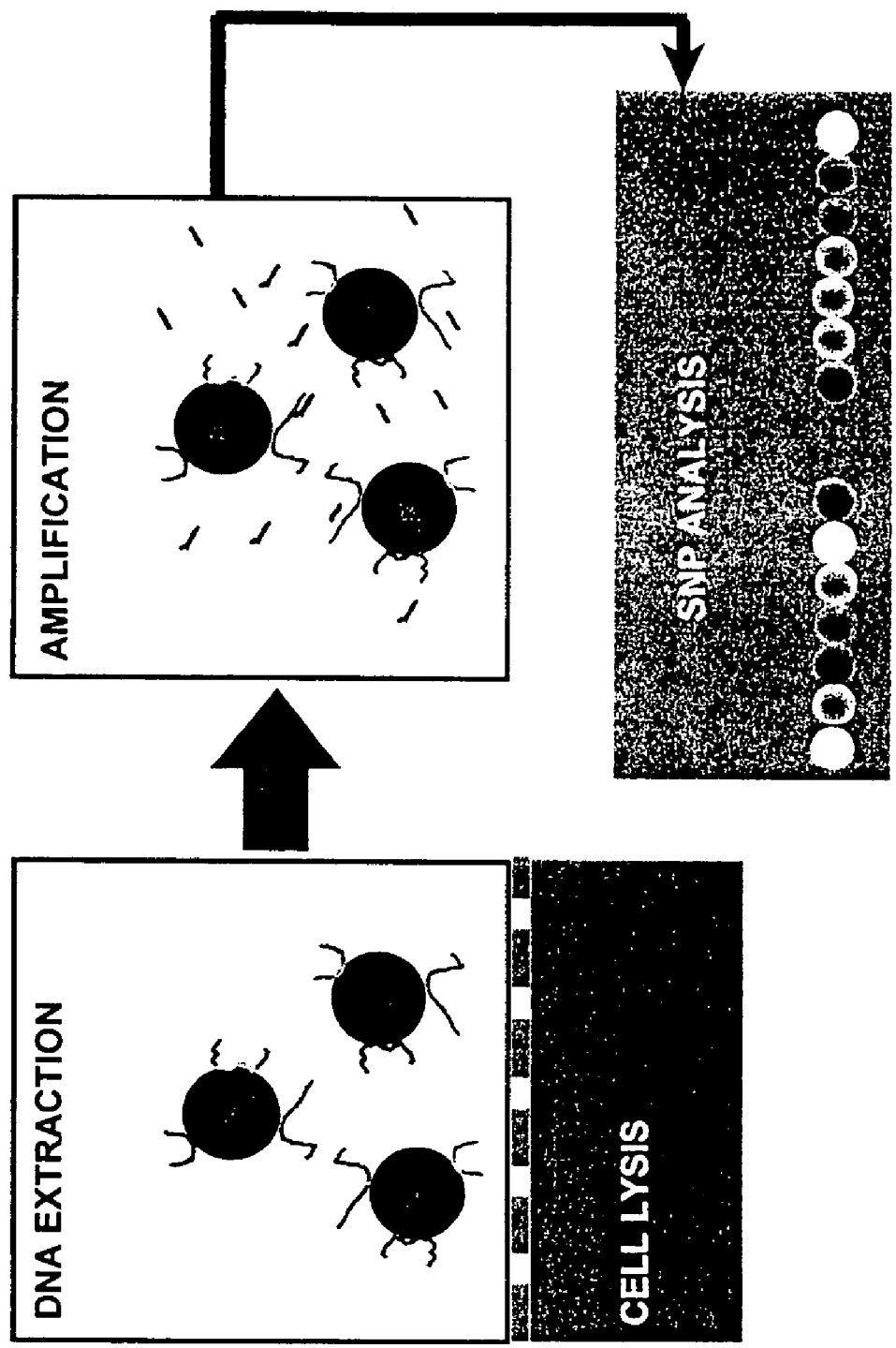
FIG. 20 is an illustration of integrated sample capture using magnetic capture beads and array-based detection using READ

For example, FIG. 20 illustrates the integration of a sequence of steps in a miniaturized format for multiplexed genotyping using a single chip with multiple compartments. First, cells are captured from a patient sample by affinity selection using functionalized magnetic beads, cells are lysed electrically or chemically in a first compartment, and genomic DNA is captured to the surface of a multiplicity of magnetic beads by non-specific binding; next, beads are collected by magnetic force into a second compartment which is in fluidic contact with the first compartment, within which the beads and DNA are washed with desired buffers; next, beads are further transferred to a location where PCR is performed using bead-coupled DNA as a template; multiple PCR strategies known in the art are available for this step [F. Fellmann, et. al., *Biotechniques*, 21:766-770]; next, PCR products released into are captured by hybridization to a pre-assembled random encoded array displaying binding agents that are specific to different polymorphisms targeted by the PCR amplification.

The use of encoded magnetic particles in conjunction with the optical programmability of LEAPS confers the ability to form reversibly immobilized arrays and to conduct programmable multi-step assay sequences under conditions in which beads are used in suspension when this is most favorable, for example to enhance reaction kinetics, and arrays are formed in real-time when this is most favorable, for example to provide a highly parallel format for imaging detection and assay read-out.

Figure 21:
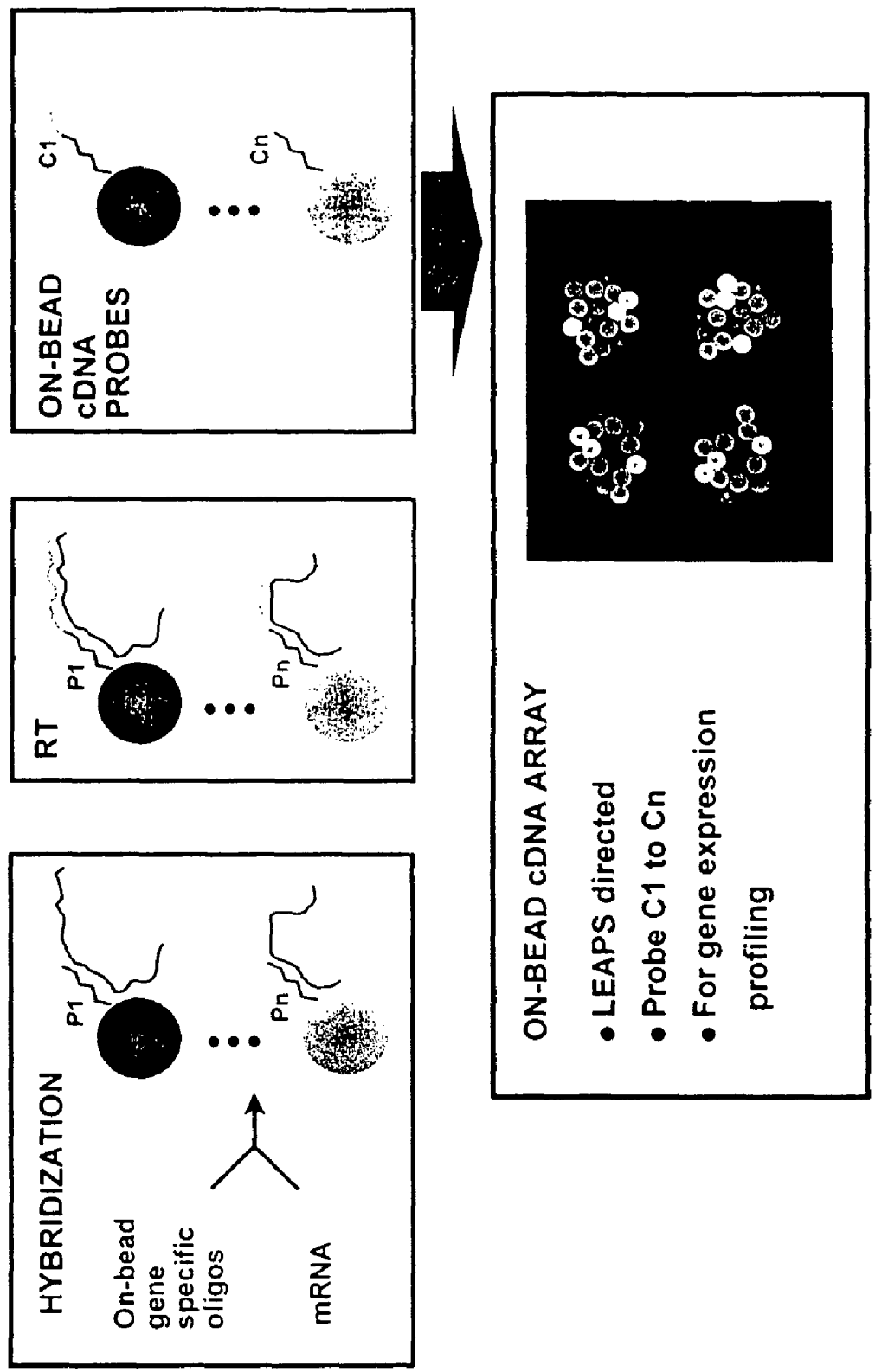
FIG. 21 is an illustration of multi-step assays using encoded magnetic beads to integrate gene-specific capture, on-bead reverse transcription and post-assay array assembly

For example, as illustrated in FIG. 21, the following sequence of steps could be integrated in a miniaturized format for the formation of a cDNA bead array. First, a pool of encoded magnetic beads, each bead type displaying a gene-specific probe, is introduced to an mRNA pool, and mRNA molecules are hybridized to their corresponding beads; next, on-bead reverse transcription (RT) is performed using bead-attached mRNA as template [E. Horenes, L. Korsnes, US 005759820]; next mRNA is released from the beads; next beads are directed to the surface of a custom-designed chip and a cDNA bead array is formed using LEAPS. Such an array could serve to display binding agents in a gene profiling experiment using another set of mRNA as the target. Alternatively, the cDNA array could be analyzed for its own expression by applying a pool of labeled DNA binding agents to profile the genes of interest within the array.

Example 16

Synthesis of Super-paramagnetic Iron Oxide $\gamma$-$Fe_2O_3$ (maghemite) Particles The synthesis was carried out in reversed micellar solutions composed of the anionic surfactant, bis(2-ethylhexyl) sodium sulfosuccinate (AOT) and isooctane (Kommareddi et al., Chem. Mater. 1996, 8, 801-809) obtained from Aldrich Chemical Co., Milwaukee, Wis. Stock solutions of 0.5M AOT were used in preparing the reversed micellar solutions containing the reactants $FeSO_4$ (Sigma Chemical Co., St. Louis, Mo.) and $NH_4OH$ (Sigma Chemical Co., St. Louis, Mo.). Specifically, 0.45 ml of 0.9M $FeSO_4$ was added to 5 ml of 0.5M AOT in isooctane, separately 0.45 ml of $NH_4OH$ was added to 5 ml of 0.5M AOT in isooctane. The reaction was initiated by adding the $NH_4OH$ reversed micellar solution to the $FeSO_4$ reversed micellar solution under vigorous stirring. The reaction was allowed to proceed for ~2-3 hrs and then the solvent was evaporated at ~40° C. to obtain a dry surfactant iron oxide composite. This composite was re-dispersed in the organic solvent of choice to give a deep red colored transparent solution.

Example 17

Synthesis of Fluorescently Colored and Magnetic Polymer Bead Composites

A stock solution of hydrophobic fluorescent dye and the iron oxide particles was made by re-dispersing the dried magnetic composite and the dye in the solvent of choice, for example a $CHCl_3$ (Aldrich Chemical Co., Milwaukee, Wis.) or $CH_2Cl_2$/$CH_3OH$ mixture (70/30 (v/v)) (Aldrich Chemical Co., Milwaukee, Wis.). A predetermined amount of polymer beads was washed thoroughly in methanol (3x) and then evaporated dry. Simultaneous incorporation of the fluorescent dye and the iron oxide nanoparticle was achieved by swelling the beads in organic solvent/nanoparticle/dye mixture. The swelling process was completed within ~1 hr. Following this the polymer beads were separated by centrifugation and washed with methanol (3x) followed by isooctane (2x) and then methanol (2x) and finally redispersed in 0.2% SDS-DI water solution.

What is claimed is:

1. A method of determining the affinity of several different analyte-binding agent interactions, in a reaction environment where several different such interactions between different analytes and binding agents take place, and where some of said analytes are capable of binding to more than one said binding agent at different affinities than where binding to other binding agents, comprising:

providing a plurality of particles comprising at least two different particle populations, wherein different particle populations have different binding agents attached thereto, and wherein the particles are associated with a distinguishable chemical or physical characteristic that identifies the binding agents on said particles, and wherein the particles are arranged in a substantially planar array on a substrate;

determining the identity of said binding agents by the distinguishable chemical or physical characteristic associated with the particles;

contacting the binding agents with an analyte molecule so as to allow the analyte to form an analyte-binding agent complex with one or more binding agents, the formation of said complex resulting in a proportional change in an optical signature associated with the particles whose binding agent is involved in the formation of the complex;

wherein said proportional change in optical signature for the analyte-binding agent complexes reflects the affinities characterizing said analyte-binding agent interactions associated with each such proportional change;

compiling a matrix of said affinities; and compiling a competitive binding interaction descriptor using a combination of the affinities in the matrix and known concentrations of analyte and binding agents participating in the formation of analyte-binding agent complexes.

2. A method of determining the affinity of several different analyte-binding agent interactions, in a reaction environment where several different such interactions between different analytes and binding agents, take place, and where some of said analytes are capable of binding to more than one said binding agent at different affinities than where binding to other binding agents, comprising:

providing a plurality of particles comprising at least two different particle populations, wherein different particle populations have different binding agents attached thereto, and wherein the particles are associated with a distinguishable chemical or physical characteristic that identifies the binding agents on said particles;

contacting the binding agents with an analyte molecule so as to allow the analyte to form an analyte-binding agent complex with one or more binding agents, the formation of said complex resulting in a proportional change in an optical signature associated with the particles whose binding agent is involved in the formation of the complex;

forming a substantially planar array of the particles on a substrate;

detecting said change in optical signature associated with said particles from the analyte-binding agent complexes which are formed;

determining the identity of said binding agents on particles in the array by the distinguishable chemical or physical characteristic associated therewith; wherein said proportional change in optical signature for the analyte-binding agent complexes reflects the affinities characterizing said analyte-binding agent interactions associated with each such proportional change;

compiling a matrix of said affinities; and compiling a competitive binding interaction descriptor using a combination of the affinities in the matrix and known concentrations of analyte and binding agents participating in the formation of analyte-binding agent complexes.

3. The method of any of claim 1 or 2, wherein the matrix obtained is used to characterize the analyte.

4. The method of claim 1 or 2, further comprising the determination of the affinity constant for the analyte-binding agent interactions, wherein the affinity constants are calculated by determining the number of analyte-binding agent complexes formed from said change in optical signature of analyte-binding agent complexes formed.

5. The method of claim 4 wherein, using the law of mass action, affinity constant K, given by the formula, $$K = \frac{[LR]}{([R_0] - [LR])[L]},$$

is determined from:

(i) said change in optical signature following formation of an analyte-binding agent complex to yield [LR], given $[L_0]$, $[R_0]$, and $n_B$, where $[L_0]$ is the initial analyte concentration, $[R_0]$ is the number of binding agents per particle and $n_B$ is the number of particles per unit volume and $$[L] = [L_0] - \frac{[LR]n_B}{N_{Av}}$$

where $N_{Av}$=Avogadro number (ii) said change in optical signature following formation of an analyte-binding agent complex to yield [LR] for at least two measurements involving different numbers, $n_B$ of particles having the same binding agent attached thereto, and given initial analyte concentration $[L_0]$: or said change in optical signature following formation of an analyte-binding agent complex to yield [LR], for at least two measurements involving different numbers of binding agent per particle, $[R_0]$ and given initial analyte concentration $[L_0]$.

6. The method of any of claim 1 or 2 wherein said change in optical signature comprises a change in the fluorescence intensity associated with the particles involved in the binding interaction.

7. The method of any one of claim 1 or 2 wherein the step of determining the identity of the binding agents in the array comprises taking a decoding image of the array that records the distinguishable chemical or physical characteristic of each particle in the array, and wherein the step of detecting the optical signature comprises taking an assay image of the array that records the change in optical signature associated with the particles having an analyte-binding agent complex.

8. The method of claim 7, wherein the assay image and the decoding image are compared using a template matching algorithm.

9. The method of any one of claim 1 or 2 wherein the planar particle array is immobilized on the substrate.

10. The method of claim 1 or 2 wherein the distinguishable chemical characteristic comprises a fluorophore tag.

11. The method of claim 1 or 2, wherein the analyte specifically binds to one binding agent but not to other binding agent(s) present.

12. The method of claim 1, wherein, using the law of mass action, the concentration of analyte [L], is determined from said change in optical signature following formation of an analyte-binding agent complex to yield [LR], given K, $n_B$ and $[R_0]$.

13. In a multi-step assay for determining the affinity constant of analyte-binding agent interactions in a reaction environment where a plurality of different such interactions between different analytes and binding agents take place, comprising:

providing a plurality of particles comprising at least two different particle populations, wherein different particle populations have different binding agents attached thereto, and wherein the particles are associated with a distinguishable chemical or physical characteristic that identifies the binding agents on said particles, and wherein the particles are arranged in a substantially planar array on a substrate;

determining the identity of said binding agents by the distinguishable chemical or physical characteristic associated with the particles;

contacting the binding agents with a first labeled analyte of interest L in a first binding reaction with a binding agent, where $[R_0]$ is the number of binding agents per particle, permitting formation of a first analyte-binding agent complex to yield $[LR]_1$, followed by injection of a second analyte L' with known affinity constant K' for the said second binding agent, wherein the affinity constant K is determined from the difference in said optical signature before and after injection of the second analyte to form a second analyte-binding agent complex so as to reduce $[LR]_1$ to $[LR]_2$ given the initial concentration of the labeled analyte, $[L_0]$ and the initial concentration of the unlabeled analyte, $[L'_0]$ and the number of binding agents per bead, $[R_0]$; where $$\frac{[LR]_1}{[LR]_2} = \frac{1 + K[L_0] + K'[L'_0]}{(1 + K[L_0])}.$$

14. The method of claim 13, wherein: using the law of mass action, the initial analyte concentration $[L_0]$ is determined from said change in optical signature following formation of an analyte-binding agent complex to yield [LR], given K, $[R_0]$, $[L'_0]$ and K'.

* * * * *